(12) United States Patent
Toll et al.

(10) Patent No.: US 9,238,053 B2
(45) Date of Patent: *Jan. 19, 2016

(54) METHODS FOR TREATMENT OF PAIN

(71) Applicant: Nocicepta LLC, Wlmington, DE (US)

(72) Inventors: Lawrence R. Toll, Redwood City, CA (US); David C. Yeomans, Sunnyvale, CA (US); Martin S. Angst, Palo Alto, CA (US); Daniel I. Jacobs, Mountain View, CA (US)

(73) Assignee: Nocicepta LLC, Wilmington, DE (US)

( * ) Notice: Subject to any disclaimer, the term of this patent is extended or adjusted under 35 U.S.C. 154(b) by 77 days.

This patent is subject to a terminal disclaimer.

(21) Appl. No.: 13/802,075

(22) Filed: Mar. 13, 2013

(65) Prior Publication Data

US 2013/0196908 A1 Aug. 1, 2013

Related U.S. Application Data

(63) Continuation of application No. 12/844,721, filed on Jul. 27, 2010, now Pat. No. 8,551,949.

(60) Provisional application No. 61/228,946, filed on Jul. 27, 2009.

(51) Int. Cl.
| | |
|---|---|
| *A61K 38/10* | (2006.01) |
| *A61K 38/00* | (2006.01) |
| *C07K 7/08* | (2006.01) |
| *C07K 7/00* | (2006.01) |
| *A61K 9/00* | (2006.01) |
| *A61K 31/485* | (2006.01) |
| *A61K 38/08* | (2006.01) |
| *A61K 45/06* | (2006.01) |

(52) U.S. Cl.
CPC .............. *A61K 38/10* (2013.01); *A61K 9/0043* (2013.01); *A61K 31/485* (2013.01); *A61K 38/08* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,837,809 A | 11/1998 | Grandy et al. | |
| 7,163,921 B1 | 1/2007 | Ishiyama et al. | |
| 7,220,725 B2 | 5/2007 | Shulov et al. | |
| 8,198,240 B2 | 6/2012 | Yeomans et al. | |
| 8,202,838 B2 | 6/2012 | Yeomans et al. | |
| 8,252,745 B2 | 8/2012 | Yeomans et al. | |
| 8,258,096 B2 | 9/2012 | Yeomans et al. | |
| 8,551,949 B2 | 10/2013 | Toll et al. | |
| 8,921,306 B2 | 12/2014 | Fairlie et al. | |
| 2004/0122013 A1 | 6/2004 | Guerrini et al. | |
| 2004/0152707 A1 | 8/2004 | Tulshian et al. | |
| 2004/0259775 A1 | 12/2004 | Kyle | |
| 2006/0063699 A1 | 3/2006 | Larsen | |
| 2007/0016968 A1 | 1/2007 | Kyrkanides et al. | |
| 2007/0054843 A1 | 3/2007 | Yeomans et al. | |
| 2007/0093420 A1 | 4/2007 | Yeomans et al. | |
| 2008/0305077 A1 | 12/2008 | Frey, II et al. | |
| 2009/0181880 A1 | 7/2009 | Yeomans et al. | |
| 2009/0291900 A1 | 11/2009 | Yeomans et al. | |
| 2011/0250212 A1 | 10/2011 | Yeomans et al. | |
| 2012/0028898 A1 | 2/2012 | Yeomans et al. | |
| 2012/0322736 A1 | 12/2012 | Yeomans et al. | |
| 2013/0196908 A1 | 8/2013 | Toll et al. | |

FOREIGN PATENT DOCUMENTS

| | | |
|---|---|---|
| EP | 1422240 A2 | 5/2004 |
| JP | 2009-506071 A | 2/2009 |
| WO | 99/03491 A1 | 1/1999 |
| WO | 03/080022 A2 | 10/2003 |
| WO | 2005/060947 A2 | 7/2005 |
| WO | 2005/060947 A3 | 9/2005 |
| WO | 2006/059105 A2 | 6/2006 |
| WO | 2006/059105 A3 | 8/2006 |
| WO | 2007/025249 A2 | 3/2007 |
| WO | 2008/025791 A1 | 3/2008 |
| WO | 2008/134071 A1 | 11/2008 |
| WO | 2011/153583 A1 | 12/2011 |

OTHER PUBLICATIONS

Extended European Search Report (includes Supplementary European Search Report and Search Opinion) received for European Patent Application No. 10806903.0, mailed on Jul. 24, 2013, 8 pages.
International Preliminary Report on Patentability received for PCT Patent Application No. PCT/US2010/043430, mailed on Feb. 9, 2012, 7 pages.
Koppert et al., "Different Profiles of Buprenorphine-Induced Analgesia and Antihyperalgesia in a Human Pain Model", Pain, vol. 118, 2005, pp. 15-22.
Lecci et al., "Nociceptin and the Micturition Reflex", Peptides, vol. 21, 2000, pp. 1007-1021.
Luo et al., "Spinal Dynorphin and Bradykinin Receptors Maintain Inflammatory Hyperalgesia", The Journal of Pain, vol. 9, No. 12, 2008, pp. 1096-1105.
Mork et al., "Does Nociceptin Play a Role in Pain Disorders in Man?", Peptides, vol. 23, 2002, pp. 1581-1587.
Ma et al., "Expression of ORL1 mRNA in Some Brain Nuclei in Neuropathic Pain Rats", Brain Research, vol. 1043, 2005, pp. 214-217.
Mansour et al., "Anatomy of CNS Opioid Receptors", Trends Neurosci, vol. 11, No. 7, 1988, pp. 308-314.
McGuire et al., "Brain Activity During Stimulus Independent Thought", NeuroReport, vol. 7, No. 13, 1996, pp. 2095-2099.
Meunier et al., "Isolation and Structure of the Endogenous Agonist of Opioid Receptor-Like ORL1 Receptor", Nature, vol. 377, 1995, pp. 532-535.

(Continued)

*Primary Examiner* — Christine J Saoud
*Assistant Examiner* — Jon M Lockard
(74) *Attorney, Agent, or Firm* — Morrison & Foerster LLP

(57) ABSTRACT

The invention provides for methods and compositions for treatment of pain via craniofacial mucosal administration of an analgesic compound (e.g. a non-opioid analgesic peptide, an NOP agonist or N/OFQ). Intranasal administration of certain analgesic peptides such as N/OFQ results in global analgesic effects.

26 Claims, 16 Drawing Sheets

(56) References Cited

OTHER PUBLICATIONS

Mika et al., "Morphine and Endomorphin-1 Differently Influence Pronociceptin/Orphanin FQ System in Neuropathic Rats", Pharmacology, Biochemistry Behavior, vol. 78, 2004, pp. 171-178.

Mogil et al., "Functional Antagonism of μ, δ and K-Opioid Antinociception by Orphanin FQ", Neuroscience Letter, vol. 214, pp. 131-134.

Neal et al., "Localization of Orphanin FQ (Nociceptin) Peptide and Messenger RNA in the Central Nervous System of the Rat", The Journal of Comparative Neurology, vol. 406, 1999, pp. 503-547.

Ossipov et al., "The Loss of Antinociceptive Efficacy of Spinal Morphine in Rats with Nerve Ligation Injury is Prevented by Reducing Spinal Afferent Drive", Neuroscience, Letters, vol. 199, 1995, pp. 87-90.

Ozaki et al., "A Potent and Highly Selective Nonpeptidyl Nociceptin/orphanin FQ Receptor (ORL1) Antagonist: J-113397", European Journal of Pharmacology, vol. 387, 2000, pp. 17-18.

Pan et al., "Cloning and Expression of a cDNA Encoding a Mouse Brain Orphanin FQ/nociceptin Precursor", Biochem. J., vol. 315, 1996, pp. 11-13.

Pasternak et al., "Minireview: Multiple Mu Opiate Receptors", Life Sciences, vol. 38, No. 21, 1986, pp. 1889-1898.

Pettit et al., "The Development of Site-Specific Drug-Delivery Systems for Protein and Peptide Biopharmaceuticals", Trends in Biotechnology, vol. 16, 1998, pp. 343-349.

Porreca et al., "Chronic Pain and Medullary Descending Facilitation", Trends in Neuroscience, vol. 25, No. 6, 2002, pp. 319-325.

Raffaeli et al., "Nociceptin Levels in the Cerebrospinal Fluid of Chronic Pain Patients with or without Intrathecal Administration of Morphine", Journal Pain Symptom Management, vol. 32. No. 4, 2006, pp. 372-377.

Reinscheid et al., "Orphanin FQ: A Neuropeptide that Activates an Opioidlike G Protein-Coupled Receptor", Science, vol. 270, 1995, pp. 792-794.

Reinscheid et al., "Structure-Activity Relationship Studies on the Novel Neuropeptide Orphanin FQ", The Journal Biological Chemistry, vol. 271, No. 24, 1996, pp. 14163-14168.

Reiss et al., "Effects of Nociceptin/Orphanin FQ Receptor (NOP) Agonist, Ro64-6198, on Reactivity to Acute Pain in Mice: Comparison to D Morphine", European Journal of Pharmacology, vol. 579, 2008, pp. 141-148.

Rizzi et al., "[Arg 14, Lys 15]Nociceptin, a Highly Potent Agonist of the Nociceptin/Orphanin FQ Receptor: in Vitro and in Vivo Studies", The Journal of Pharmacology and Experimental Therapeutics, vol. 300, No. 1, 2002, pp. 57-63.

Rizzi et al., "In Vitro and in Vivo Studies on UFP-112, a Novel Potent and Long Lasting Agonist Selective for the Nociceptin/Orphanin FQ Receptor", Peptides, vol. 28, No. 6, 2007, pp. 1240-1251.

Sayani et al., "Systemic Delivery of Peptides and Proteins Across Absorptive Mucosae", Crit Rev Ther Drug Carrier Syst, vol. 13, 1996, pp. 85-184.

Sherman et al., "Morphine Insensitive Allodynia is Produced by Intrathecal Strychnine in the Lightly Anesthetized Rat", Pain, vol. 56, 1994, pp. 17-29.

Shimohigashi et al., "Sensitivity of Opioid Receptor-Like Receptor ORL 1 for Chemical Modification on Nociceptin, a Naturally Occurring Nociceptive Peptide", The Journal of Biological Chemistry, vol. 271, No. 39, 1996, pp. 23642-23645.

Spagnolo et al., "Pharmacological Characterization of the Nociceptin/Orphanin FQ Receptor Antagonist SB-612111 [(−)-cis-1-Methyi-7-[[4-2,6-Dichlorophenyl)Piperidin-1-yi]Methyi]-6,7,8,9-Tetrahydro-5H-Benzocyclohepten-5-ol]: in vitro Studies", The Journal of Pharmacology and Experimental Therapeutics, vol. 321, No. 3, 2007, pp. 961-967.

Stevens et al., "Nociceptin Produces Antinociception After Spinal Administration in Amphibians", Pharmacology, Biochemistry and Behavior, vol. 91, 2009, pp. 436-440.

Tavani et al., "Role of Peripheral Mu, Delta and Kappa Opioid Receptors in Opioid-Induced Inhibition of Gastrointestinal Transit in Rats", The Journal of Pharmacology and Experimental Therapeutics, vol. 254, No. 1, 1990, pp. 91-97.

Thorne et al., "Delivery of Insulin-Like Growth Factor-I to the Rat Brain and Spinal Cord along Olfactory and Trigeminal Pathways following Intranasal Administration", Neuroscience, vol. 127, 2004, pp. 481-496.

Tian et al., "Bidirectional Modulatory Effect of Orphanin FQ on Morphine-Induced Analgesia: Antagonism in Brain and Potentiation in Spinal Cord of the Rat", British Journal of Pharmacology, vol. 120, 1997, pp. 676-680.

Toyoshima et al., "Expression of Calbindin-D28K by Reactive Astrocytes in Gerbil Hippocampus After Ischaemia", NeuroReport, vol. 7, No. 13, 1996, pp. 2087-2091.

Wang et al., "Distinct Effect of Intracerebroventricular and Intrathecal Injections of Nociceptin/Orphanin FQ in the Rat Formalin Test", Regulatory Peptides, vol. 79, 1999, pp. 159-163.

Wang et al., "Parenteral Formulations of Proteins and Peptides: Stability and Stabilizers", Journal of Parenteral Science & Technology, vol. 42, 1988, pp. S4-S26.

Wang et al., "Review of Excipients and pH's for Parenteral Products Used in the United States", Journal of the Parenteral Drug Association, vol. 34, No. 6, 1980, pp. 452-462.

Williams et al., "Nociceptin and Urotensin-II Concentrations in Critically Ill Patients with Sepsis", British Journal of Anaesthesia, vol. 100, No. 6, 2008, pp. 810-814.

Xie et al., "Hypocretin/Orexin and Nociceptin/Orphanin FQ Coordinately Regulate Analgesia in a Mouse Model of Stress-Induced Analgesia", The Journal of Clinical Investigation, vol. 118, No. 7, 2008, pp. 2471-2481.

Xu et al., "Nociceptin or Antinociceptin: Potent Spinal Anti nociceptive Effect of Orphanin FQ/nociceptin in the Rat", NeuroReport, vol. 7, No. 13, 1996, pp. 2092-2094.

Xue et al., "Studies and Progress on Orphanin FQ," Foreign Medical Sciences, Section of Pathophysiology and Clinical Medicine, vol. 23, No. 2, 2003, pp. 158-161.

Yamada et al., "Pharmacological Profiles of a Novel Opioid Receptor-Like1 (ORL1) Receptor Antagonist, JTC-801", British Journal Pharmacology, vol. 135, 2002, pp. 323-332.

Yamamoto et al., "Effects of Intrathecally Administered Nociceptin, an Opioid Receptor-Like1 (ORL1) Receptor Agonist, on the Thermal Hyperalgesia Induced by Unilateral Constriction Injury to the Sciatic Nerve in the Rat", Neuroscience Letters, vol. 224, 1997, pp. 107-110.

Yeomans et al., "Nociceptive Responses to High or Low Rates of Noxious Cutaneous Heating are Mediated by Different Nociceptors in the Rat: Behavioral Evidence", Pain, vol. 68, 1996, pp. 133-140.

Zaratin et al., "Modification of Nociception and Morphine Tolerance by the Selective Opiate Receptor-Like Orphan Receptor Antagonist (−)-cis-1-Methyl-7-[[4-(2,6-Dichlorophenyi)Piperidin-1-yl] Methyl]-6,7,8,9-Tetrahydro-5 H-Benzocyclohepten-5-ol (SB-612111)", The Journal of Pharmacology and Experimental Therapeutics, vol. 308, No. 2, 2004, pp. 454-461.

Zaveri et al., "Small-Molecule Agonists and Antagonists of the Opioid Receptor-Like Receptor (ORL 1, NOP): Ligand-Based Analysis of Structural Factors Influencing Intrinsic Activity at NOP", The AAPS Journal, vol. 7, No. 2, Article 34, 2005, pp. E345-E352.

International Search Report received for PCT Patent Application No. PCT/US2010/043430, mailed on Oct. 15, 2010, 4 pages.

Written Opinion received for PCT Patent Application No. PCT/US2010/043430, mailed on Oct. 15, 2010, 5 pages.

Non Final Office Action received for U.S. Appl. No. 12/844,721, mailed on Mar. 1, 2013, 12 pages.

Notice of Allowance received for U.S. Appl. No. 12/844,721, mailed on Jun. 10, 2013, 8 pages.

Anonymous, "Welcome to IASP", located at <http://www.iasp-pain.org//AM/Template.cfm?Section=Home>, last visited on Feb. 7, 2011, 2 pages.

Armstead, W. M., "Role of Nociceptin/Orphanin FQ in the Physiologic and Pathologic Control of the Cerebral Circulation", Exp. Biol. Med., vol. 227, 2002, pp. 957-968.

Bartosz-Bechowski et al., "Novel Nociceptin Analogues", Acta Biochimica Polonica, vol. 48, No. 4, 2001, pp. 1155-1158.

(56) References Cited

OTHER PUBLICATIONS

Bartsch et al., "The ORL-1 (NOP1) Receptor Ligand Nociceptin/Orphanin FQ (N/OFQ) Inhibits Neurogenic Dural Vasodilatation in the Rat", Neuropharmacology, vol. 43, 2002, pp. 991-998.
Berzetei-Gurske et al., "Determination of Activity for Nociceptin in the Mouse Vas Deferens", European Journal Pharmacology, vol. 302, 1996, 2 pages.
Bigoni et al., "Characterization of Nociceptin Receptors in the Periphery: In Vitro and in Vivo Studies", Naunyn Schmiedebergs Arch Pharmacol, vol. 359, 1999, pp. 160-167.
Borgland et al., "Nociceptin Inhibits Calcium Channel Currents in a Subpopulation of Small Nociceptive Trigeminal Ganglion Neurons in Mouse", The Journal of Physiology, vol. 536, No. 1, 2001, pp. 35-47.
Brennan et al., "Characterization of a Rat Model of Incisional Pain", Pain, vol. 64, 1996, pp. 493-501.
Briscini et al., "Up-Regulation of ORL-1 Receptors in Spinal Tissue of Allodynic Rats After Sciatic Nerve Injury", European Journal of Pharmacology, vol. 447, 2002, pp. 59-65.
Calo et al., "[Nphe1,Arg14,Lys15]Nociceptin-NH2, A Novel Potent and Selective Antagonist of the Nociceptin/Orphanin FQ Receptor", British Journal of Pharmacology, vol. 136, No. 2, 2002, pp. 303-311.
Calo et al., "Characterization of [Nphe1]Nociceptin(1-13)NH2, A New Selective Nociceptin Receptor Antagonist", British Journal of Pharmacology, vol. 129, No. 6, 2000, pp. 1183-1193.
Calo et al., "Pharmacology of Nociceptin and Its Receptor: a Novel Therapeutic Target", British Journal of Pharmacology, vol. 129, No. 7, 2000, pp. 1261-1283.
Carra et al., "[(pF)Phe4,Arg14,Lys15]N/OFQ-NH2 (UFP-102), A Highly Potent and Selective Agonist of the Nociceptin/Orphanin FQ Receptor", The Journal of Pharmacology and Experimental Therapeutics, vol. 312, No. 3, 2005, pp. 1114-1123.
Carvalho et al., "The Nociceptin/Orphanin FQ-NOP Receptor Antagonist Effects on an Animal Model of Sepsis", Intensive Care Med, vol. 34, 2008, pp. 2284-2290.
Champion et al., "Experimental Biology Symposium on Autonomic and Cardiovascular Regulation: Focus on Nociceptin and Opioid Peptides. Role of Nitric Oxide in Mediating Vasodilator Responses to Opioid Peptides in the Rat", Clinical and Experimental Pharmacololgy Physiology, vol. 29, 2002, pp. 229-232.
Chaplan et al., "Quantitative Assessment of Tactile Allodynia in the Rat Paw", Journal Neuroscience Methods, vol. 53, 1994, pp. 55-63.
Chiou et al., "Nociceptin/Orphanin FQ Peptide Receptors: Pharmacology and Clinical Implications", Current Drug Targets, vol. 8, No. 1, 2007, pp. 117-135.
Chu et al., "Inhibition of Cardiovascular Activity Following Microinjection of Novel Opioid-Like Neuropeptide Nociceptin (Orphanin FQ) into the Rat Rostral Ventrolateral Medulla", Brain Research, vol. 829, 1999, pp. 134-142.
Connor et al., "Nociceptin Receptor Coupling to a Potassium Conductance in Rat Locus Coeruleus Neurones in Vitro", British Journal of Pharmacology, vol. 119, 1996, pp. 1614-1618.
Courteix et al., "Evidence for an Exclusive Antinociceptive Effect of Nociceptin/Orphanin FQ, an Endogenous Ligand for the ORL1 Receptor, in Two Animal Models of Neuropathic Pain", Pain, vol. 110, 2004, pp. 236-245.
Cox et al., "Opioid Receptors: Introduction", IUPHAR Database, located at <http://www.iuphar-db.org/DATABASE/FamilyIntroductionForward?familyID=50>, last visited on Feb. 24, 2010, Oct. 13, 2009, 4 pages.
Darland et al., "Orphanin FQ/Nociceptin: A Role in Pain and Analgesia, But So Much More,", Trends Neurosci, vol. 21, No. 5, 1998, pp. 215-221.
Dixon, W. J., "Staircase Bioassay: The Up-and-Down Method", Neurosci Biobehav Rev, vol. 15, No. 1, 1991, pp. 47-50.
Ertsey et al., "Plasma Nociceptin Levels are Reduced in Migraine without Aura", Cephalalgia, vol. 25, 2004, pp. 261-266.
Fernandez et al., "Nociceptin/Orphanin FQ Increases Anxiety-Related Behavior and Circulating Levels of Corticosterone During Neophobic Tests of Anxiety", Neuropsychopharmacology, vol. 29, 2004, pp. 59-71.

Fu et al., "Changes in Expression of Nociceptin/Orphanin FQ and its Receptor in Spinal Dorsal Horn During Electroacupuncture Treatment for Peripheral Inflammatory Pain in Rats", Peptides, vol. 28, 2007, pp. 1220-1228.
Gintzler et al., "Modulation of Enkephalin Release by Nociceptin (Orphanin FQ)", European Journal of Pharmacology, vol. 325, 1997, pp. 29-34.
Giuliani et al., "The Inhibitory Effect of Nociceptin on the Micturition Reflex in Anaesthetized Rats", British Journal of Pharmacology, vol. 124, 1998, pp. 1566-1572.
Gwak et al., "Analgesic Effects of Intra-Nasal Enkephalins", Journal of Pharmacy and Pharmacology, vol. 55, 2003, pp. 1207-1212.
Hawkinson et al., "Opioid Activity Profiles Indicate Similarities Between the Nociceptin/Orphanin FQ and Opioid Receptors", European Journal of Pharmacology, vol. 389, 2000, pp. 107-114.
Hou et al., "Nociceptin Immunoreactivity and Receptor mRNA in the Human Trigeminal Ganglion", Brain Research, vol. 964, 2003, pp. 179-186.
Hruby et al., "Conformation-Activity Relationships of Opioid Peptides with Selective Activities at Opioid Receptors", Biopolymers (Peptide Science), vol. 51, 1999, pp. 391-410.
Jenck et al., "A Synthetic Agonist at the Orphanin FQ/Nociceptin Receptor ORL1: Anxiolytic Profile in the Rat", Proc Natl Acad Sci, vol. 97, No. 9, 2000, pp. 4938-4943.
Jenck et al., "Orphanin FQ Acts as an Anxiolytic to Attenuate Behavioral Responses to Stress", Proc Natl Acad Sci, vol. 94, 1997, pp. 14854-14858.
Kapusta et al., "Cardiovascular and Renal Responses Produced by Central Orphan in FQ/Nociceptin Occur Independent of Renal Nerves", Am Journal Physiology Regulatory Integrative Computer Physiology, vol. 46, 1999, pp. 987-995.
Kapusta et al., "Neurohumoral Effects of Orphanin FQ/Nociceptin: Relevance to Cardiovascular and Renal Function", Peptides, vol. 21, 2000, pp. 1081-1099.
Khroyan et al., "Activity of New NOP Receptor Ligands in a Rat Peripheral Mononeuropathy Model: Potentiation of Morphine Anti-Allodynic Activity by NOP Receptor Antagonists", European Journal of Pharmacology, vol. 610, 2009, pp. 49-54.
Khroyan et al., "Anti-Nociceptive and Anti-Allodynic Effects of a High Affinity NOP Hexapeptide [Ac-RY(3-CI)YRWR-NH2] (Syn 1020) in Rodents", European Journal Pharmacology, vol. 560, 2007, pp. 29-35.
Knoflach et al., "Modulation of Voltage-Gated Calcium Channels by Orphanin FQ in Freshly Dissociated Hippocampal Neurons", The Journal of Neuroscience, vol. 16, No. 21, 1996, pp. 6657-6664.
Ko et al., "Behavioral Effects of a Synthetic Agonist Selective for Nociceptin/Orphanin FQ Peptide Receptors in Monkeys", Neuropsychopharmacology, vol. 34, No. 9, 2009, pp. 2088-2096.
Ko et al., "Quantitative Analysis of Nociceptin in Blood of Patients with Acute and Chronic Pain", NeuroReport, vol. 13, No. 16, 2002, pp. 1631-1633.
Kolczewski et al., "Novel Hexahydrospiro[Piperidine-4, 1'-Pyrrolo[3,4-c]Pyrroles]: Highly Selective Small-Molecule Nociceptin/Orphanin FQ Receptor Agonists", Journal of Medicinal Chemistry, vol. 46, No. 2, 2003, pp. 255-264.
Kotlinska et al., "Non-Peptidergic OP4 Receptor Agonist Inhibits Morphine Antinociception but Does Not Influence Morphine Dependence", NeuroReport, vol. 14, No. 4, 2003, pp. 601-604.
Lazzeri et al., "Daily Intravesical Instillation of 1 mg Nociceptin/Orphanin FQ for the Control of Neurogenic Detrusor Overactivity: A Multicenter Placebo Controlled, Randomized Exploratory Study", The Journal of Urology, vol. 176, 2006, pp. 2098-2102.
Lazzeri et al., "Urodynamic and Clinical Evidence of Acute Inhibitory Effects of Intravesical Nociceptin/Orphanin FQ on Detrusor Overactivity in Humans: A Pilot Study", The Journal of Urology, vol. 166, 2001, pp. 2237-2240.
Lazzeri et al., "Urodynamic Effects of Intravesical Nociceptin/Orphanin FQ in Neurogenic Detrusor Overactivity: A Randomized, Placebo-Controlled, Double-Blind Study", Urology, vol. 61, No. 5, 2003, pp. 946-950.
Spagnolo B., "Activities of mixed NOP and u-opioid receptor ligands", British Journal of Pharmacology 153, 2008, pp. 609-619.

METHODS FOR TREATMENT OF PAIN

CROSS-REFERENCE TO RELATED APPLICATIONS

This application is a continuation of U.S. patent application Ser. No. 12/844,721, filed Jul. 27, 2010, now U.S. Pat. No. 8,551,949, which claims priority to U.S. Provisional Patent Application No. 61/228,946, filed Jul. 27, 2009, the disclosures of which are hereby incorporated by reference in their entirety.

STATEMENT OF RIGHTS TO INVENTIONS MADE UNDER FEDERALLY SPONSORED RESEARCH

The present invention was made in part under NIH Grant No. 1R43DE020816-01. The United States government may have certain rights in this invention.

BACKGROUND OF THE INVENTION

Pain is a perception mediated by the activation of certain brain structures. Pain is usually initiated when specialized neurons, termed nociceptors, which innervate the skin or other peripheral tissue, are activated by mechanical, thermal, chemical or other noxious stimuli. Pain is also experienced when peripheral or central neuronal structures involved in the processing of pain become hyperactive, e.g. as a result of trauma, ischemia or inflammation. Other causes of pain include disease-specific processes, metabolic disturbances, muscle spasm, and the onset of a neuropathic event or syndrome.

Pain treatment of almost any type usually includes one or more analgesic drugs which are usually classified into three groups: primary non-opioid, opioid, and co-analgesics, also known as adjuvants. Non-opioid analgesic drugs include acetaminophen and non-steroidal anti-inflammatory drugs or NSAIDs. These drugs can be effective for treating mild to moderate pain, but may have significant side-effects such as liver damage in the case of acetaminophen and gastric ulcers in the case of NSAIDs. Opioid drugs, sometimes referred to as "narcotics", include natural substances such as opium, opium-derived substances, such as morphine, and semi-synthetic and synthetic substances, such as fentanyl. Co-analgesic medications are drugs that typically address indications other than pain relief, but possess analgesic action for certain painful conditions. An example of a co-analgesic drug is gabapentin, which has a primary indication for the treatment of epilepsy, but also is effective in treating some kinds of neuropathic pain.

Opioid drugs are commonly used to relieve moderate to severe pain. However, their usefulness is limited by tolerance and dependence that normally develop with chronic treatment. Opioid drugs such as morphine can be addictive and are associated with significant and potentially fatal side effects such as respiratory depression in addition to sedation and mental alteration, constipation, nausea, exaggerated pain sensitivity, hormonal disturbances, and alteration of the immune system.

Despite a wide range of available medical treatments, pain continues to afflict millions of individuals in the US alone and remains a profound burden to patients, health care, and business. New methods are required for increasing the efficacy of intervention and reducing the side effects associated with pain management in the clinical setting.

BRIEF SUMMARY OF THE INVENTION

Disclosed are methods and compositions for treatment of pain by craniofacial mucosal administration of an NOP agonist, for example, intranasal administration of nociceptin/orphanin FQ (N/OFQ).

In one aspect, the invention provides a method for the treatment of pain comprising administering to an individual in need thereof an effective dose of an NOP agonist via craniofacial mucosal administration. In some embodiments, the treatment comprises treatment of a trigeminal pain, a somatic pain, a neuropathic pain, a procedural pain or a visceral pain. In some embodiments, the treatment comprises treatment of an acute pain or a chronic pain. In some embodiments, the pain is a craniofacial pain or a head pain. In some embodiments, the craniofacial pain or the head pain is caused by temporomandibular joint disorder (TMJ), migraine or trigeminal neuralgia. In some embodiments, the craniofacial mucosal administration comprises intranasal administration, buccal administration, sublingual administration or conjunctival administration. In a particular embodiment, the mucosal administration is intranasal administration. In some embodiments, the NOP agonist is administered to the lower two thirds of the nasal cavity. In some embodiments, the NOP agonist is administered to the upper third of the nasal cavity. In some embodiments, the NOP agonist is administered specifically to reach both the lower two thirds and the upper third of the nasal cavity. In some embodiments, the NOP agonist is administered via buccal or sublingual administration. In some embodiments, the NOP agonist is administered via conjunctival administration or via other tissues around the eye. In a particular embodiment, the NOP agonist is N/OFQ. In some embodiments, any of the methods may further comprise administering to the individual in need thereof at least one additional active agent, wherein the additional active agent is administered before, after or simultaneously with administration of the NOP agonist. In some embodiments, the methods may further comprise administering to the individual in need thereof at least two additional active agents, wherein each of the additional active agents is administered independently before, after or simultaneously with administration of the NOP agonist.

In another aspect, the invention provides a method for the treatment of pain comprising administering to an individual in need thereof an effective dose of an non-opioid analgesic peptide via craniofacial mucosal administration, wherein said administration results in a global analgesic effect. In some embodiments, the treatment comprises alleviation of pain. In some embodiments, the treatment comprises prevention of pain. In some embodiments, the craniofacial mucosal administration comprises intranasal administration, buccal administration, sublingual administration or conjunctival administration. In a particular embodiment, the craniofacial mucosal administration is intranasal administration.

In one aspect, the invention provides a method for the treatment of pain comprising administering to an individual in need thereof an effective dose of N/OFQ via intranasal administration. In some embodiments, the unit dose of the N/OFQ administered is about 0.2 mg to about 5000 mg. In some embodiments, the administration results in reduction of a pain rating on the VAS of 30% or more.

In another aspect, the invention provides methods for the treatment or prevention of migraine headache pain or the treatment of migraine comprising administering to an individual in need thereof an effective dose of an NOP agonist wherein the NOP agonist is administered via craniofacial mucosal administration, e.g. intranasal administration. In some embodiments, the treatment comprises treating one or more symptoms associated with migraine such as nausea, photophobia and phonophobia. In some embodiments, the migraine is a migraine without aura, a migraine with aura or a migraine with aura but without headache. In a particular embodiment, the method for the treatment of migraine comprises administering to an individual in need thereof an effective dose of N/OFQ via intranasal administration.

Pharmaceutical compositions comprising an analgesic compound (e.g. a non-opioid analgesic peptide, an NOP agonist or N/OFQ) and methods for administrating such compositions via craniofacial mucosal administration (e.g. intranasal administration, buccal administration, sublingual administration or conjunctival administration) are also provided. As are kits comprising the pharmaceutical compositions and optionally a device for administration. The pharmaceutical composition may further comprise one or more pharmaceutically acceptable excipients, adjuvants, diluents or stabilizers. In some embodiments, the pharmaceutical composition or the kits may include one or more additional active agents such as at least one additional analgesic agent, a vasoconstrictor, at least one protease inhibitor and/or at least one absorption enhancer.

In another aspect, provided is the use of an analgesic compound (e.g. a non-opioid analgesic peptide, an NOP agonist or N/OFQ) or a pharmaceutical composition comprising an analgesic compound (e.g. a non-opioid analgesic peptide, an NOP agonist or N/OFQ) for the manufacture of a medicament for the treatment of pain via craniofacial mucosal administration (e.g. intranasal administration). Also provided is an analgesic compound (e.g. a non-opioid analgesic peptide, an NOP agonist or N/OFQ) for use in the treatment of pain via craniofacial mucosal administration (e.g. intranasal administration).

DETAILED DESCRIPTION OF THE INVENTION

Figure 1:
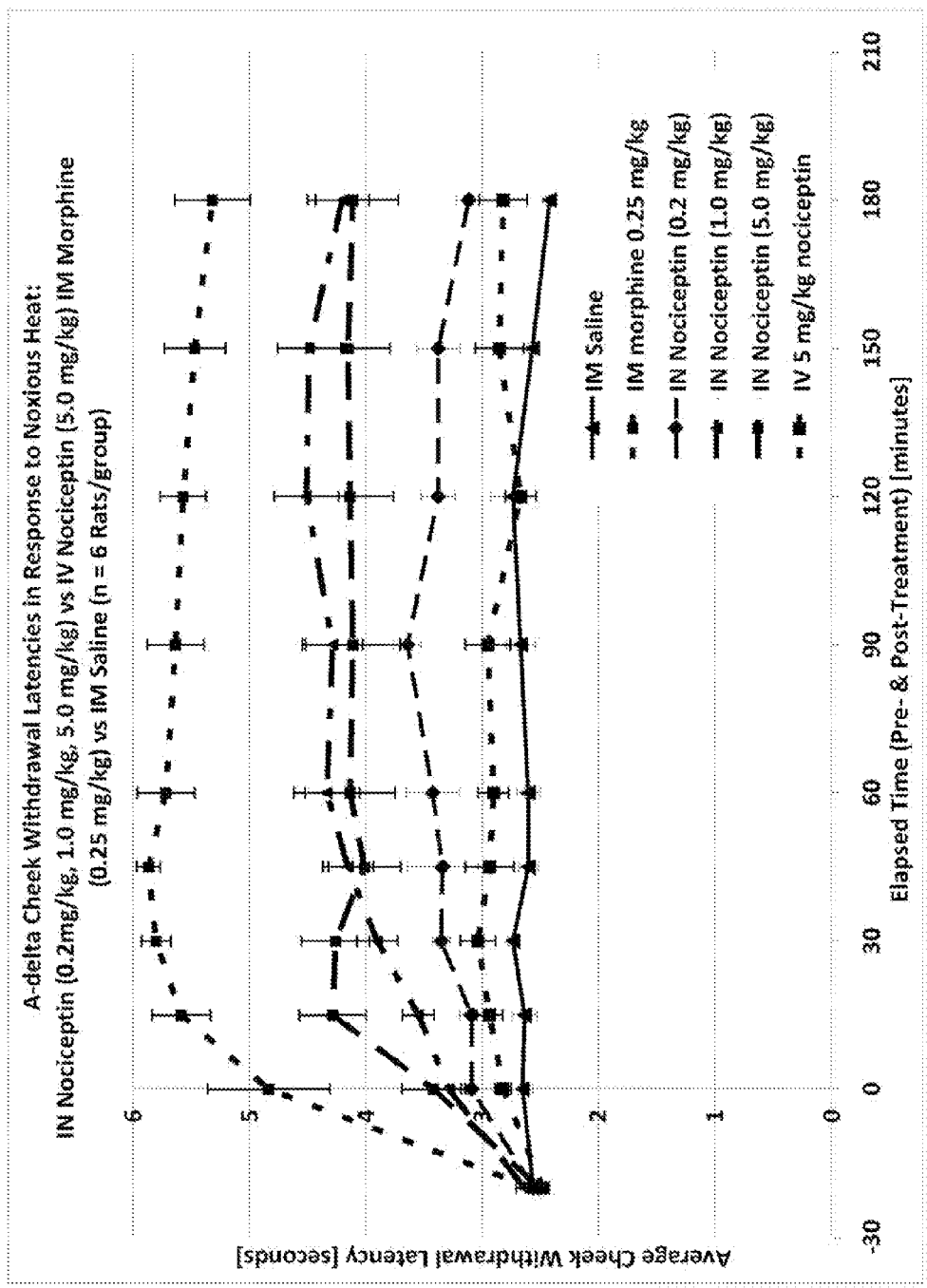
FIG. 1 shows A-delta cheek withdrawal latencies in response to noxious heat: i.n. Nociceptin (0.2 mg/kg, 1.0 mg/kg, and 5.0 mg/kg) vs. i.v. Nociceptin (5.0 mg/kg) vs. i.m. Morphine (0.25 mg/kg) vs. i.m. Saline. Data are presented as the mean±1 SEM. (n=6 Rats/group).

The invention provides, inter alia, compositions and methods for treatment of pain by administration of analgesic compounds, such as the craniofacial mucosal administration of a non-opioid analgesic peptide, polypeptide, or protein (e.g. nociceptin/orphanin FQ (N/OFQ) or other non-opioid molecules.

DEFINITIONS

Although analgesia in the strictest sense is an absence of pain, as used herein, "analgesia" refers to reduction in pain perceived by an individual.

"Analgesia agent", "analgesic agent" or "analgesic" refers to any biomolecule, drug or active agent that alleviates or prevents pain.

"Acute pain" refers to sudden pain from a specific cause (injury, infection, inflammation, etc.) that has lasted for a limited period of time (as opposed to chronic pain). "Chronic pain" refers to a persistent state of pain. Chronic pain is often associated with long-term incurable or intractable medical conditions or diseases. "Procedural pain" refers to pain arising from a medical, dental surgical or other procedure wherein the procedure may be planned or associated with acute trauma.

"Headache disorder" includes migraine, tension headache, cluster headache, trigeminal neuralgia, secondary headaches, and miscellaneous-type headaches.

"Migraine" includes migraine headache, migraine without aura, migraine with aura, and migraine with aura but without headache.

"Systemic side effects" include, but are not limited to, cardiovascular including peripheral vasodilation and inhibition of baroreceptors; dermatologic including pruritus (itching), flushing and red eyes; gastrointestinal including nausea and vomiting, decreased gastric motility, decreased biliary, pancreatic and intestinal secretions and delays in food digestion, diminished peristaltic waves in large intestine contributing to constipation, epigastric distress or biliary colic in biliary tract; respiratory including depressed respiratory effort; and urinary including urinary urgency and difficulty with urination; and peripheral limb heaviness.

"Central nervous system side effects" or "CNS side effects" include, but are not limited to, narcosis, euphoria, drowsiness, apathy, psychotic ideation, mental confusion, alteration in mood, reduction in body temperature, feelings of relaxation, dysphoria (an emotional state characterized by anxiety, depression, or unease), and nausea and vomiting (caused by direct stimulation of chemoreceptors in the medulla).

"Global analgesic effect" refers to an effect on any part of the body. A global analgesic effect can be achieved with or without systemic circulation of an active agent. For example, a global analgesic effect can be achieved by intranasal administration of nociceptin that may not result in significant systemic circulation of the N/OFQ peptide.

"Craniofacial mucosal administration" refers to delivery to the mucosal surfaces of the nose, nasal passageways, nasal cavity; the mucosal surfaces of the oral cavity including the gingiva (gums), the floor of the oral cavity, the lips, the tongue; and the mucosal surfaces of or around the eye including the conjunctiva, the lacrimal gland, the nasolacrimal ducts, and the mucosa of the upper or lower eyelid and the eye.

"Intranasal administration" or "administered intranasally" refers to delivery to the nose, nasal passageways or nasal cavity by spray, drops, powder, gel, film, inhalant or other means.

The "inferior region of the nasal cavity" refers generally to the portion of the nasal cavity where the middle and inferior turbinate bones protrude and is a region of the nasal cavity that is significantly innervated by the trigeminal nerve. The "superior region of the nasal cavity" is defined by the upper third and cribriform plate region wherein olfactory innervation is located.

Analgesic Compounds

Nociceptin/orphanin FQ (N/OFQ) is a 17 amino acid peptide with a molecular weight of 1809 in the opioid peptide family. The amino acid sequence of human N/OFQ is FGG-FTGARKSARKLANQ (SEQ ID No:1). It binds to a G-protein coupled receptor originally called ORL1, now officially named NOP receptor. Although the NOP receptor is a protein in the opioid receptor family, opioids do not bind with high affinity to NOP receptors; neither does N/OFQ bind with high affinity to opioid receptors. Therefore, N/OFQ is considered a non-opioid peptide. When N/OFQ was first discovered and tested in mice by the intracerebroventricular (i.c.v.) route of administration, it was found to reduce tail flick and hotplate latency in mice. This indicated that, unlike the opioid peptides, N/OFQ is nociceptive, rather than antinociceptive. Further studies by several groups demonstrated that i.c.v. N/OFQ blocked opioid analgesia mediated by each of the opioid receptors. However, when administered intrathecally (i.t.) N/OFQ potentiated morphine analgesia or was analgesic on its own. This indicates that the site of administration of N/OFQ is important to its ultimate actions. When the first NOP receptor antagonists were designed, they were tested in i.c.v. administration and found to possess antinociceptive activity.

Like the other members of the opioid receptor family, NOP receptors are $G_{i/o}$ coupled. Without wishing to be bound by any particular theories, activation of NOP receptors may lead to a decrease in cellular cAMP levels and it also inhibits G-protein coupled receptor potassium channels (Girk Channels). This may lead to a hyperpolarization of the cells on which the receptor resides and a reduction in cellular activity. N/OFQ may act in the brain by reducing neuronal activity, which may result in an attenuation of the actions of endogenous or exogenous opioids, thereby disinhibiting pain pathways. In the spinal cord, the cellular localization may be such that it acts as an analgesic, similarly to the opioids, although the mechanism of action may be different.

NOP receptors and N/OFQ are found in many regions throughout the brain, and consequently have many central nervous system actions. One region that has a large number of NOP receptors is the trigeminal ganglion. This is also a brain region that mediates craniofacial and head pain due to a variety of conditions including temporomandibular joint disorder (TMJ), migraine, trigeminal neuralgia, etc.

Intranasal administration of N/OFQ might concentrate in the trigeminal ganglia and reduce the activity of those neurons. Although the effect of such neuronal suppression could not be known without testing, one possibility was regional antinociception. Alternatively, it was unknown whether N/OFQ would reach a concentration high enough in other parts of the brain that it would inhibit the analgesic response as seen in i.c.v. administration of N/OFQ. Given that N/OFQ has diverse functions, being hyperalgesic in some regions of the CNS and analgesic in other regions of the CNS and the periphery, it was unpredictable what the overall effect of N/OFQ would be after intranasal administration.

Figure 2:
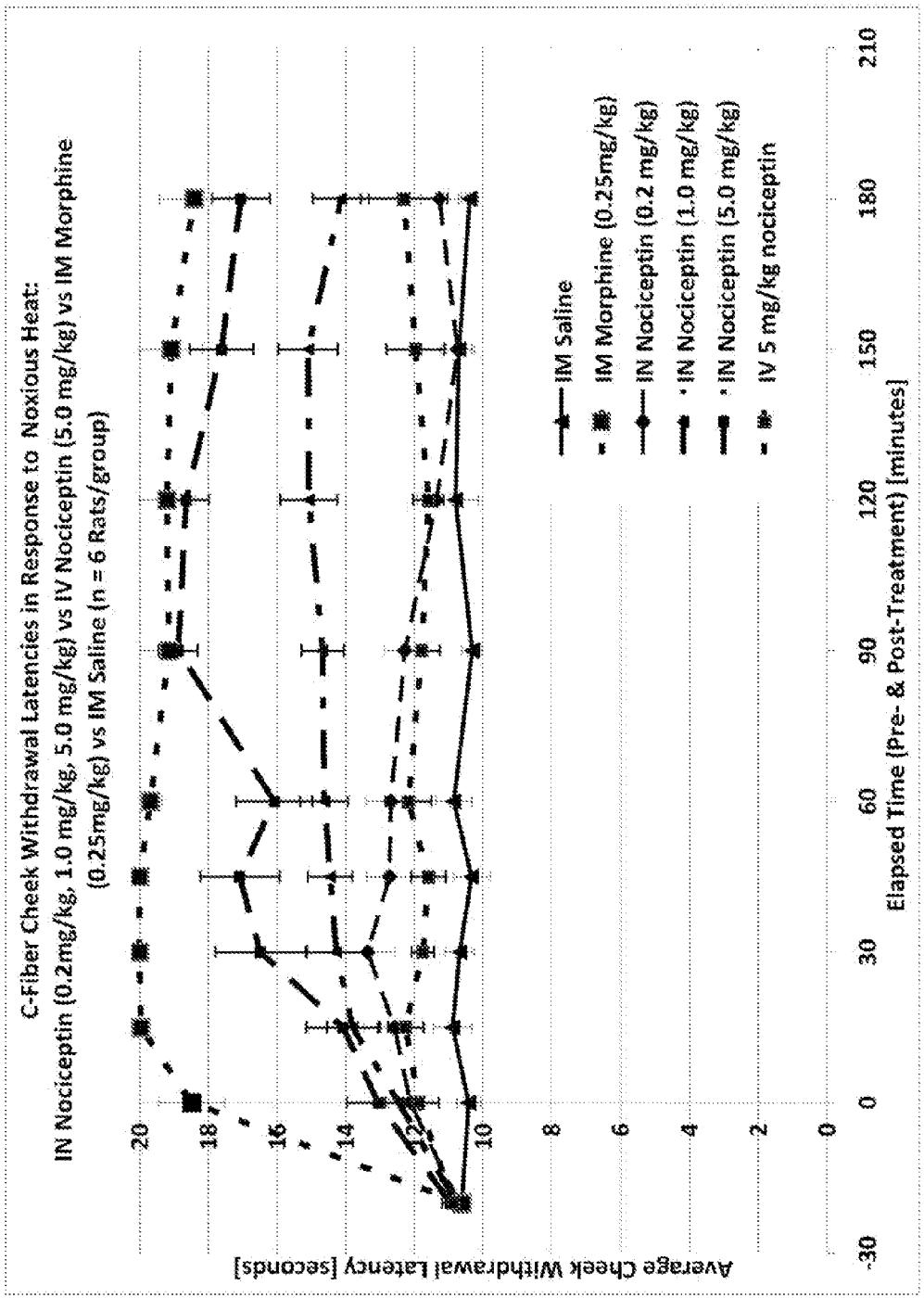
FIG. 2 shows C-fiber cheek withdrawal latencies in response to noxious heat: i.n. Nociceptin (0.2 mg/kg, 1.0 mg/kg, and 5.0 mg/kg) vs. i.v. Nociceptin (5.0 mg/kg) vs. i.m. Morphine (0.25 mg/kg) vs. i.m. Saline. Data are presented as the mean±1 SEM. (n=6 Rats/group).
Figure 3:
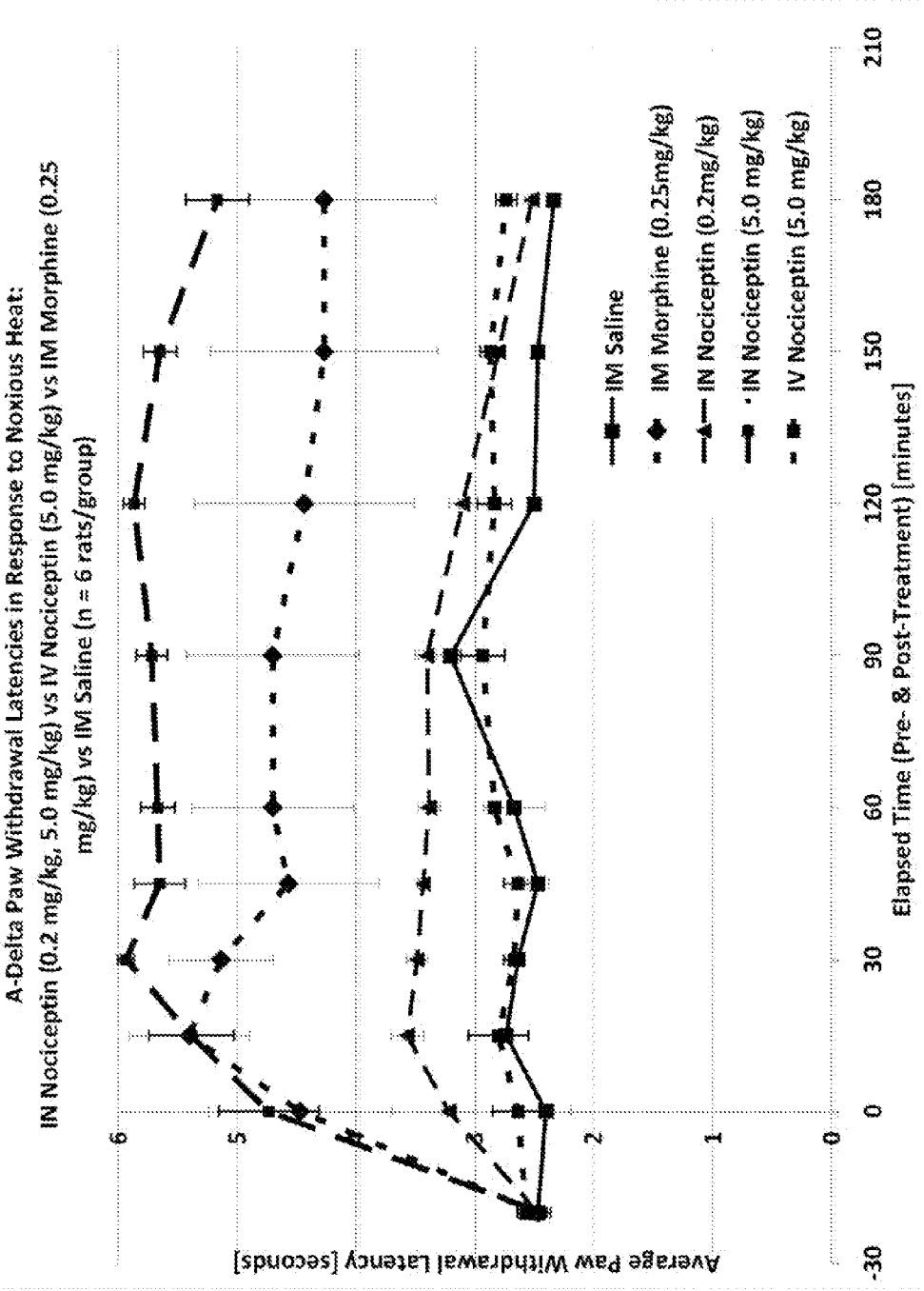
FIG. 3 shows A-delta paw withdrawal latencies in response to noxious heat: i.n. Nociceptin (0.2 mg/kg, 5.0 mg/kg) vs. i.v. Nociceptin (5.0 mg/kg) vs. i.m. Morphine (0.25 mg/kg) vs. i.m. Saline. Data are presented as the mean±1 SEM. (n=6 rats/group).
Figure 4:
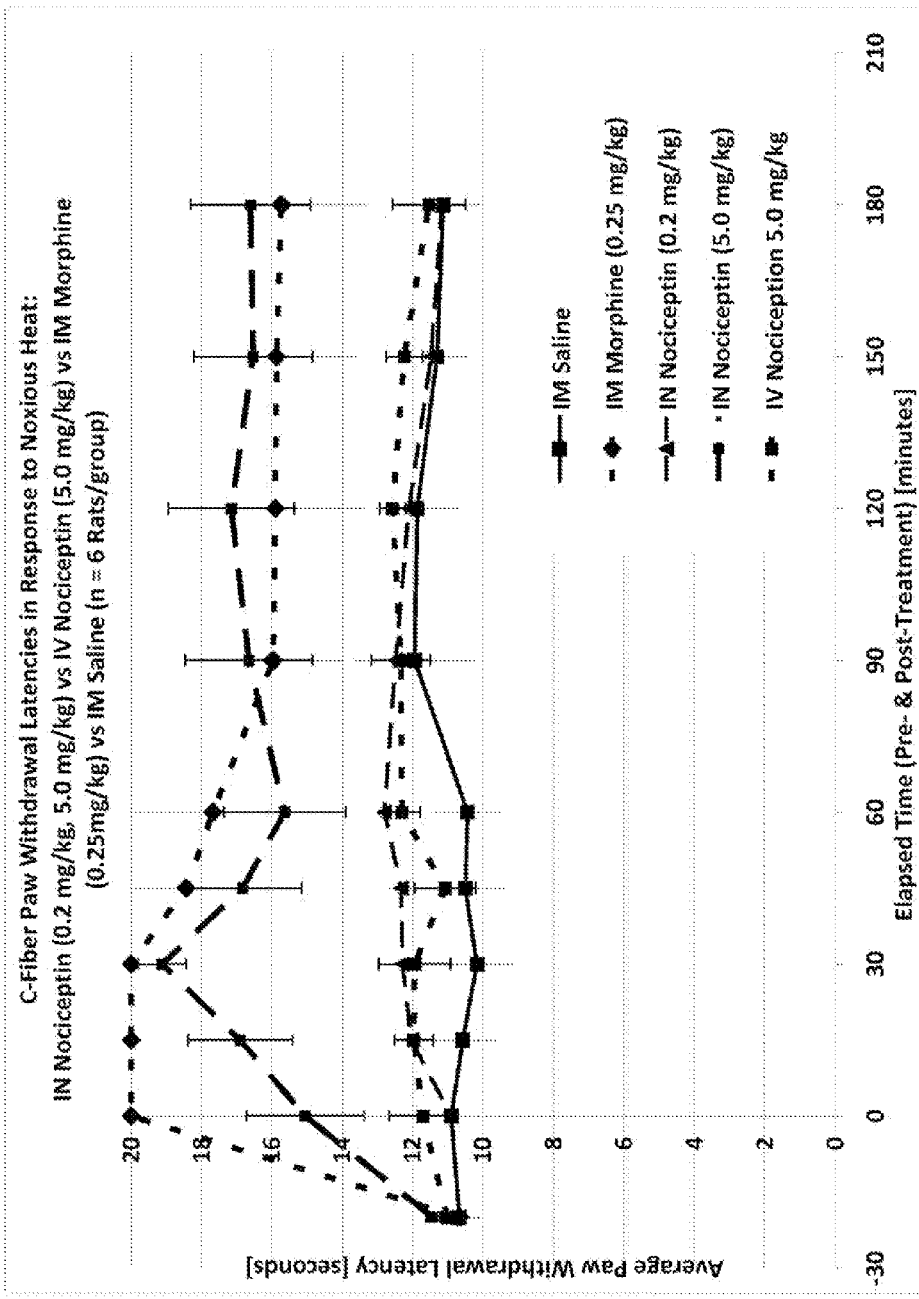
FIG. 4 shows C-fiber paw withdrawal latencies in response to noxious heat: i.n. Nociceptin (0.2 mg/kg, 5.0 mg/kg) vs. i.v. Nociceptin (5.0 mg/kg) vs. i.m. Morphine (0.25 mg/kg) vs. i.m. Saline. Data are presented as the mean±1 SEM. (n=6 Rats/group).

In a thermal nociception model in rats, N/OFQ administered intranasally demonstrated a dose dependent analgesic effect on heat induced pain in the face for both A-delta and C-fiber pain threshold tests, while N/OFQ showed little or no effect when administered intravenously (FIGS. 1 and 2). This demonstrates that the analgesic effect of intranasal N/OFQ is not a result of systemic circulation. A more surprising result was observed in experiments where the heat induced pain was applied to the hindpaws of rats. Intranasal N/OFQ showed a dose dependent analgesic effect on heat induced pain in the hindpaw in both A-delta and C-fiber pain threshold tests (FIGS. 3 and 4). Intravenous nociceptin showed little or no effect in the paw experiments. Thus, when administered intranasally, N/OFQ shows not only a regional analgesic effect for pain (e.g. in the face), but also a global analgesic effect, while the same dose administered systemically (e.g. i.v. administration) shows little or no analgesic effect. The fact that i.n. nociceptin produces a global analgesic effect, whereas systemic nociceptin does not, may imply that i.n. N/OFQ may be activating a descending pain modulatory system. Provided in the invention, therefore, is a method for treating pain using intranasal N/OFQ wherein the intranasal administration results in a global analgesic effect.

Also useful in the methods of the invention are agonists for the NOP receptor or NOP agonists including peptide and non-peptide compounds. Examples of peptide NOP agonists include but are not limited to N/OFQ, truncated N/OFQ analogs (Reinscheid, R. K. et al, *J. Biol. Chem.* (1996) 271: 14163-14168), N/OFQ agonist peptides such as UFP-102, UFP-112 (Carra, G. et al, *J. Pharmacol. Exp. Ther.* (2005) 312:1114-1123; Rizzi, A. et al, *Peptides* (2007) 28:1240-1251), and NOP agonist hexapeptides such as Syn 1020 (Khroyan, T. V. et al. *Eur. J. Pharmacol.* (2007) 560:29-35). Example of small molecule NOP agonists include hexahydrospiro[piperidine-4,1'-pyrrolo[3,4-c]pyrroles] (Kolczewski, S. et al, *J. Med. Chem.* (2003) 46:255-264) and other non-peptide NOP agonists described herein.

While intranasal, transconjunctival, and transbuccal delivery has been proposed for various analgesic molecules as a method of treating head and orofacial pain (US 20070093420, US 20070054843), to date, there is no evidence of the effect of intranasal, transbuccal, or transconjunctival delivery of NOP agonists on pain.

Many peptides are known to be analgesic. They are administered via various routes to provide local, regional and/or global analgesia. One class of analgesic peptide, referred to as "opioid peptides," has an opioid receptor binding moiety and the capacity to bind with high affinity to an opioid receptor. An opioid peptide can be a naturally occurring endogenous peptide, fragments, analogues or derivatives thereof. An opioid peptide can also be a non-endogenous peptide, fragments, analogues or derivatives thereof. Examples of opioid peptides are endorphins, enkephalins, dynorphins, dermorphins, dermenkephalins, morphiceptin, endomorphins, dalargin, and other synthetic mu, delta, and kappa agonist peptides.

As used herein, "non-opioid analgesic peptide" refers to an analgesic peptide that alleviates or prevents pain by a mechanism other than high-affinity binding to an opioid receptor, or a peptide that has lower affinity for an opioid receptor than molecules generally considered to be opiates or opioids. For example, an analgesic peptide that has low binding affinity (e.g. less than about 1 μM or less than about 10 μM) for μ-, δ-, and κ-opioid receptors is considered a non-opioid analgesic peptide.

Unless specifically noted otherwise, "binding affinity" as used herein is measured as the dissociation constant ($K_d$) with a unit of measure of molar concentration (M), which correspond to the concentration of ligand at which the binding site on a particular protein is half occupied, i.e. the concentration of ligand, at which the concentration of receptor with ligand bound, equals the concentration of receptor with no ligand bound. The smaller the dissociation constant, the more tightly bound the ligand is, or the higher the affinity between ligand and protein. For example, a ligand with a nanomolar (nM) dissociation constant binds more tightly to a particular protein than a ligand with a micromolar (μM) dissociation constant. When a ligand has a binding affinity of less than 1 μM for a receptor, the dissociation constant for the ligand-receptor binging is greater than 1 μM.

Examples of non-opioid analgesic peptides useful in the methods of the invention include but are not limited to hypocretins/orexins, calcitonin, octreotide, somatostatin, vasopressin, galanin, the C-fragment of lipotropin and Ac-rfwink-$NH_2$, omega-conotoxin GV1A, omega-conotoxin MVIIA, peptide antagonists of pro-nociceptive peptide neurotransmitter receptors CGRP1 and CGRP2, such as CGRP 8-37 and CGRP 28-3; peptide antagonists of pro-nociceptive peptide neurotransmitter receptor NK1, including N-acetyl tryptophan, D-Pro9-[Spiro-y-lactam]-Leu 10,Trp 11-Physalaemin(1-11), Tyr-D-Phe-Phe-D-His-Leu-Met-$NH_2$ (Sendide) and spantide II; peptide antagonists of pro-nociceptive peptide neurotransmitter receptor NK2, including PhCO-Ala-Ala-D-Trp-Phe-D-Pro-Pro-Nle-$NH_2$ (GR98400), [Tyr5, D-Trp6,8,9,Lys10]-NKA (4-10) (MEN10376) and derivatives thereof; peptide antagonists of pro-nociceptive peptide neurotransmitter receptors VPAC2, VPAC1 and PAC1, including VIP(6-28), Ac His(1) [D-Phe(2), K(15), R(16), L(27)] VIP (3-7)/GRF (8-27).

U.S. Pat. No. 7,220,725 discloses use of pyroglutamate containing tripeptides and tetrapeptides in an ointment, cream or salve for treatment of pain. Intranasal administration of tripeptides and tetrapeptides disclosed in U.S. Pat. No. 7,220,725 for treating pain is provided herein. Proteins that can provide analgesic effect can also be useful in the methods provided herein, such as brain-derived neurotrophic factor (BDNF), nerve growth factor (NGF), neurotrophin-3 (NT-3), botulinum toxin, and anti-inflammatory cytokines (e.g. interleukin-4, interleukin-10 and interleukin-13.)

Compounds useful in performing the methods of the invention can be evaluated using the appropriate tests known in the art such as human clinical studies and tests in animal models for pain treatment. In some embodiments, the compound useful in the methods of the invention demonstrates a global analgesic effect when administered via craniofacial mucosal administration such as intranasal administration. In some embodiments, the compound useful in the methods of the invention demonstrates a stronger analgesic effect when administered via intranasal administration compared to intravenous administration. In some embodiments, the compound shows little or no analgesic effect when administered via intravenous administration. In some embodiments, craniofacial mucosal administration of the compound useful in the methods of the invention results in insignificant blood circulation of the compound. In some embodiments, craniofacial mucosal administration of the compound useful in the methods of the invention results in certain blood circulation of the compound. In some embodiments, craniofacial mucosal administration of the compound does not cause significant CNS side effects.

Pain

Pain is an unpleasant sensory and emotional experience associated with actual or potential tissue damage, or described in terms of such damage (www.iasp-pain.org), and categorized in Table 1 as suggested by the International Association for the Study of Pain.

TABLE 1

| Pain location | Affected Organ System | Time course | Severity (intensity/time) | Etiology |
|---|---|---|---|---|
| 1. Head, face, mouth<br>2. Cervical<br>3. Upper shoulder, limbs<br>4. Thoracic region<br>5. Abdominal region<br>6. Lower back, lumbar spine, sacrum, coccyx<br>7. Lower limbs<br>8. Pelvic region<br>9. Anal, perineal, genital region | 1. Central nervous system (e.g. post stroke)<br>2. Peripheral nervous system (e.g. diabetic neuropathy)<br>3. Autonomic nervous system<br>4. Special senses (e.g. auditory or visionary; e.g. glaucoma)<br>5. Respiratory system<br>6. Cardiovascular system<br>7. Skeletal system<br>8. Muscle system<br>9. Connective tissue<br>10. Cutaneous system<br>11. Gastrointestinal system<br>12. Genitourinary system<br>13. Visceral system | 1. Single episode, limited duration<br>2. Continuous or nearly continuous, non-fluctuating<br>3. Continuous or nearly continuous, non-fluctuating<br>4. Recurring irregularly (e.g. headache)<br>5. Recurring regularly (e.g. premenstrual pain)<br>6. Paroxysmal (e.g. tic douloureux)<br>7. Sustained with superimposed paroxysm | 1. mild acute<br>2. mild chronic<br>3. moderate acute<br>4. moderate chronic<br>5. severe acute<br>6. severe chronic | 1. Genetic<br>2. Congenital<br>3. Trauma, surgery, Interventional, burns<br>4. Infective, parasitic<br>5. Inflammatory non-infective<br>6. Immune reaction<br>7. Neoplasm<br>8. Toxic<br>9. Neuropathic |

Pain treatable using methods of the invention includes any pain described herein, such as a pain having any combination of attributes listed in Table 1.

In some aspects, the invention provides methods for the treatment of pain by craniofacial mucosal administration (e.g. intranasal administration, buccal administration, sublingual administration or conjunctival administration) of an analgesic compound (e.g. a non-opioid analgesic peptide, an NOP agonist or N/OFQ). In some embodiments, the pain is a somatic pain. In some embodiments, the pain is a superficial somatic pain. In some embodiments, the pain is a deep somatic pain. In some embodiments, the pain is a musculoskeletal pain. In some embodiments, the pain is a visceral pain. In some embodiments, the pain is a neuropathic pain. In some embodiments, the pain is a head pain or a craniofacial pain. In some embodiment, the pain is a perioperative/periprocedural pain. In some embodiments, the invention provides a safe and effective treatment of pain without causing severe sedation, respiratory depression and/or addiction.

In some embodiments, the invention provides methods for the treatment of an acute pain by craniofacial mucosal administration (e.g. intranasal administration, buccal administration, sublingual administration or conjunctival administration) of an analgesic compound (e.g. a non-opioid analgesic peptide, an NOP agonist or N/OFQ). Acute pain examples include but are not limited to traumatic pain, procedural (surgery, dental, dermatologic, etc.) pain, wound care pain, headaches (migraine, cluster, etc.), musculoskeletal/spine pain (e.g. back pain), earache, toothache, ischemic (e.g., cardiac) pain, and pain caused by acute glaucoma, GI diseases (cholecystitis, intestinal torsion, appendicitis, etc.), urologic diseases (stones, testicular torsion, etc.), spasm, infection, inflammation (gout, lupus, etc.), toxins (insect, animal, etc.), sore throat, menstrual cycle and childbirth.

In some embodiment, the non-opioid analgesic peptide, NOP agonist or N/OFQ, attenuates sharp and shooting pain associated with movement. This type if pain is poorly covered by opioids but is highly significant in the perioperative setting. In some embodiments, the non-opioid analgesic peptide, NOP agonist or N/OFQ is delivered intranasally for the treatment of acute procedural pain such as pain experienced during or after surgery (e.g. in patients undergoing major surgical procedures such as arthroplasty of the hip and knee).

In some embodiments, the invention provides methods for the treatment of a chronic pain by craniofacial mucosal administration (e.g. intranasal administration, buccal administration, sublingual administration or conjunctival administration) of an analgesic compound (e.g. a non-opioid analgesic peptide, an NOP agonist or N/OFQ). Chronic pain examples include but are not limited to fibromyalgia, arthritis pain, cancer pain, musculoskeletal/spine pain (including back pain), temporomandibular joint disorder (TMJD or TMJ), trigeminal neuralgia, chronic headaches, complex regional pain syndrome (types I and II), pain associated with neurologic diseases (MS, diabetic neuropathy, etc.), neuroma, pelvic inflammatory disease, endometriosis, shingles and postherpetic neuralgia, and infection (e.g., HIV) associated chronic neuropathy, chemotherapy-induced neuropathic pain, surgery-induced neuropathic pain, trauma-induced neuropathic pain, vulvodynia, atypical craniofacial pain, radiculopathy/sciatica, phantom limb, odontalgia and burning mouth syndrome.

Migraine and Head Pain

Head pain can arise from a variety of medical conditions including but not limited to, primary headaches such as migraine, cluster headache, tension or stress headache, chronic daily headache, secondary headaches caused by specific conditions such as neoplastic and infectious diseases, toxin ingestion or over-consumption of alcohol and trigeminal neuralgia. As discussed herein, the most common type of primary vascular headache is migraine with cluster headache being less common but equally debilitating. Tension or "stress"-type headaches are believed to be the most common headache type overall in regard to the largest number of individuals affected. The characteristics of these headaches or headache disorders have been described in the HIS and are summarized in Table 2.

TABLE 2

|  | Migraine | Tension | Cluster | Trigeminal Neuralgia |
| --- | --- | --- | --- | --- |
| Pathophysiology | Trigemino-vascular pathway | Myo-facial pathway | Trigemino-autonomic pathway | Trigeminal nerve pathway |
| Laterality | Unilateral (60%) | Bilateral | Unilateral (100%) | Unilateral |
| Intensity | Moderate to severe | Mild to Moderate | Severe | Severe |
| Pain Characteristic | Pulsating (50%) | Pressing | Boring, piercing | Stabbing, Electric shock-like |
| Duration | 4-72 hours | Minutes to days | 15-180 minutes Several per day | 1-2 seconds to 2 minutes Many per day |
| Physical Activity Effect | Aggravated by activity | No effect | Patients are restless | Minor movements can bring on attack |
| Associated Symptoms | Nausea Photophobia Phonophobia |  | Conjunctival injection Lacrimation Nasal congestion Rhinorrhea Facial sweating Miosis Ptosis Eyelid edema |  |

Headache pain and trigeminal neuralgia are often not effectively treated with current medications and new methods for pain relief are needed. Accordingly, some aspects of the present invention include methods for treatment of headache pain or trigeminal neuralgia by administration of an effective amount of an NOP agonist wherein the administration results in analgesia to the craniofacial or head region. The NOP agonist can be administered to a patient with a headache disorder including, but not limited to, migraine, cluster headache, tension headache, secondary types of headache and trigeminal neuralgia.

In some aspects, the invention provides a method for treating migraine or other headache comprising administering to an individual in need thereof an effective dose of an analgesic compound (e.g. a non-opioid analgesic peptide, an NOP agonist or N/OFQ) via craniofacial mucosal administration (e.g. intranasal administration, buccal administration, sublingual administration or conjunctival administration). In some embodiments, the invention provides a method for treating migraine comprising administering to an individual in need thereof an effective dose of N/OFQ via intranasal administration. In some embodiments, the method comprises treatment of migraine headache, migraine without aura, migraine with aura, migraine with aura but without headache, basilar type migraine, familial hemiplegic migraine, sporadic hemiplegic migraine, abdominal migraine, acephalgic migraine or menstrual migraine. In some embodiment, the treatment comprises alleviating or preventing one or more symptoms associated with migraine. In some embodiments, the symptom is a prodrome phase symptom, an aura phase symptom, a pain phase symptom or a postdrome phase symptom. In some embodiments, the treatment comprises alleviating or preventing one or more symptoms selected from nausea, photophobia and phonophobia.

Methods

In one aspect, provided herein are methods for treating an individual for pain, comprising: administering to the individual an effective amount of an analgesic compound or a pharmaceutical composition comprising an analgesic compound through a craniofacial mucosal route. Some aspects of the invention include methods wherein the analgesic compound includes, but is not limited to a peptide, an amino acid, a polypeptide, or a small molecule compound which has analgesic properties. In some embodiments, the analgesic compound is a non-opioid analgesic peptide. In some embodiments, the analgesic compound is an analgesic peptide that alleviates or prevents pain by a mechanism other than high affinity binding to an opioid receptor. In some embodiments, the analgesic compound is a peptide that has lower affinity for an opioid receptor than molecules generally considered to be opiates or opioids. In some embodiments, the analgesic compound is an analgesic peptide that has binding affinity of less than 10 mM, less than 1 mM, less than 0.1 mM, less than 10 µM or less than 1 µM for µ-, δ-, and κ-opioid receptors.

In some embodiments, the analgesic compound is a non-opioid analgesic peptide selected from the group consisting of hypocretins/orexins, calcitonin, octreotide, somatostatin, vasopressin, galanin, the C-fragment of lipotropin and Ac-rfwink-NH$_2$, omega-conotoxin GV1A, omega-conotoxin MVIIA, peptide antagonists of pro-nociceptive peptide neurotransmitter receptors CGRP1 and CGRP2, such as CGRP 8-37 and CGRP 28-3; peptide antagonists of pro-nociceptive peptide neurotransmitter receptor NK1, including N-acetyl tryptophan, D-Pro9-[Spiro-y-lactam]-Leu 10,Trp 11-Physalaemin(1-11), Tyr-D-Phe-Phe-D-His-Leu-Met-NH$_2$ (Sendide) and spantide II; peptide antagonists of pro-nociceptive peptide neurotransmitter receptor NK2, including PhCO- Ala-Ala-D-Trp-Phe-D-Pro-Pro-Nle-NH$_2$ (GR98400), [Tyr5, D-Trp6,8,9,Lys10]-NKA (4-10) (MEN10376) and derivatives thereof; peptide antagonists of pro-nociceptive peptide neurotransmitter receptors VPAC2, VPAC1 and PAC1, including VIP(6-28), Ac His(1) [D-Phe(2), K(15), R(16), L(27)] VIP (3-7)/GRF (8-27). In some embodiments, the analgesic compound is a pyroglutamate containing tripeptide or tetrapeptide disclosed in U.S. Pat. No. 7,220,725. In some embodiments, the analgesic compound is a polypeptide such as a brain-derived neurotrophic factor (BDNF), a nerve growth factor (NGF), a neurotrophin-3 (NT-3), a botulinum toxin, or an anti-inflammatory cytokines (e.g. interleukin-4, interleukin-10 and interleukin-13.)

In some embodiments, the analgesic compound is an NOP receptor agonist. In some embodiments, the analgesic compound is a peptide NOP agonist selected from N/OFQ, truncated N/OFQ analogs, N/OFQ agonist peptides such as UFP-102, UFP-112, and NOP agonist hexapeptides such as Syn 1020. In some embodiments, the analgesic compound is a non-peptide NOP agonist such as hexahydrospiro[piperidine-4,1'-pyrrolo[3,4-c]pyrroles] and other small molecule NOP agonists described herein. In a particular embodiment, the analgesic compound is N/OFQ (nociceptin).

In some embodiments, provided is a method for the treatment of pain comprising administering to an individual in need thereof an effective dose of a non-opioid analgesic peptide (e.g. N/OFQ) via craniofacial mucosal administration. Craniofacial mucosal administration includes but is not limited to intranasal administration, buccal administration, sublingual administration and conjunctival administration. In some embodiments, prophylactic mucosal administration of a non-opioid analgesic peptide prevents or delays the onset of pain. In some embodiments, mucosal administration of a non-opioid analgesic peptide alleviates or reduces the severity of pain. In some embodiments, the pain is a somatic pain. In some embodiments, the pain is a superficial somatic pain. In some embodiments, the pain is a deep somatic pain. In some embodiments, the pain is a musculoskeletal pain. In some embodiments, the pain is a visceral pain. In some embodiments, the pain is a neuropathic pain. In some embodiments, the pain is a head pain or a craniofacial pain. In some embodiments, the pain is a chronic pain such as a chronic pain described herein. In some embodiments, the pain is an acute pain such as an acute pain described herein. In some embodiments, the pain is a pain associated with migraine, a cluster headache, a tension headache, a secondary type of headache or trigeminal neuralgia. In some embodiments, the pain is caused by TMJ, migraine or trigeminal neuralgia. In some embodiment, the pain is a sharp and shooting pain associated with movement. In some embodiments, the pain is a neuropathic pain is caused by surgery related nerve injury.

In some embodiments, the method comprises administering an analgesic compound (e.g. a non-opioid analgesic peptide, an NOP agonist or N/OFQ) or a pharmaceutical composition comprising an analgesic compound (e.g. a non-opioid analgesic peptide, an NOP agonist or N/OFQ) to an individual via craniofacial mucosal administration for treatment of migraine-associated pain, a cluster headache pain or a trigeminal neuralgia pain. In some embodiments, the method comprises abortive treatment for migraine-associated pain comprising administering via a craniofacial mucosal route an analgesic compound or a pharmaceutical composition comprising an analgesic compound to an individual experiencing a migraine or other headache pain. In some embodiments, the method comprises prophylactic treatment for migraine-associated pain comprising administering via a craniofacial mucosal route an analgesic compound or a pharmaceutical composition comprising an analgesic compound to an individual to prevent onset of a migraine headache. In some embodiments, the method comprises prophylactic treatment for migraine-associated pain comprising administering via a craniofacial mucosal route an analgesic compound or a pharmaceutical composition comprising an analgesic compound to an individual experiencing a migraine-associated aura prior to onset of a migraine headache. In some embodiments, the methods comprise prophylactic treatment for cluster headache pain comprising administering via a craniofacial mucosal route an analgesic compound or a pharmaceutical composition comprising an analgesic compound to an individual after a cluster series has started but prior to successive headaches in the cluster series. In some embodiments, the methods comprise prophylactic treatment for trigeminal neuralgia pain comprising administering via a craniofacial mucosal route an analgesic compound or a pharmaceutical composition comprising an analgesic compound to an individual after trigeminal neuralgia attack but prior to successive attacks.

In one aspect, the invention provides a method for the treatment of pain comprising administering to an individual in need thereof an effective dose of an analgesic compound (e.g. a non-opioid analgesic peptide, an NOP agonist or N/OFQ) via craniofacial mucosal administration, wherein said administration results in a global analgesic effect. In studies of the analgesic effect of intranasal N/OFQ peptide in animals, we have observed longer cheek withdrawal latencies (indicative of both. A-delta and C fiber analgesia) after intranasal (i.n.) administration of N/OFQ when compared to saline administered controls, but did not observe significant analgesia after intravenous (i.v.) administration of N/OFQ at the same dosage. Similar analgesic effects on paw withdrawal responses were observed when N/OFQ was administered i.n. compared to saline controls, but not for i.v. administration. In one embodiment of the invention, an analgesic peptide such as N/OFQ is administered via intranasal administration to achieve global analgesic effect. In some embodiments, craniofacial mucosal administration (e.g. intranasal administration) of the analgesic compound (e.g. N/OFQ) results in a stronger analgesic effect compared to intravenous administration of the compound. In some embodiments, craniofacial mucosal administration of the analgesic compound does not cause significant systemic side-effects. In some embodiment, the non-opioid analgesic peptide such as N/OFQ is administered via intranasal administration where the majority of the non-opioid peptide (e.g. N/OFQ) that reaches the brain is delivered to the brain without entering the systemic circulation.

In one aspect, the invention provides a method for the treatment of pain in an individual comprising administering to the individual an analgesic compound (e.g. a non-opioid analgesic peptide such as N/OFQ, or another NOP agonist) to mucosal tissue or epithelium within the oral cavity, the nasal cavity, within or around the eye or to the skin. The oral mucosal tissues include, but are not limited to, the gingiva (gums), the floor of the oral cavity, the lips, tongue, or a combination thereof. The methods can include administering an analgesic compound to conjunctiva or other mucosal tissues around the eye. The tissues or epithelium include, but are not limited to, the conjunctiva, the lacrimal gland, the nasolacrimal ducts, the mucosa of the upper or lower eyelid, the eye, or a combination thereof. A compound or a pharmaceutical composition that is administered to the conjunctiva but not absorbed completely through the conjunctival mucosa can drain through the nasolacrimal ducts into the nose wherein it can be absorbed by mucosal tissue within the nasal cavity. In some embodiments, the analgesic compound is a non-opioid peptide. In some embodiments, the analgesic compound is a peptide or non-peptide NOP agonist. In a particular embodiment, the analgesic compound is an N/OFQ peptide. The analgesic compound can be administered to the mucosa tissue within the nasal cavity. Suitable regions include, but are not limited to, the inferior two-thirds of the nasal cavity, or the upper third, or the entire nasal passage. In some embodiments, the NOP agonist (such as a peptide NOP agonist, e.g. N/OFQ) is administered to the upper third of the nasal cavity. In some embodiments, the NOP agonist (such as a peptide NOP agonist, e.g. N/OFQ) is administered to the lower two thirds of the nasal cavity. In some embodiments, the NOP agonist (such as a peptide NOP agonist, e.g. N/OFQ) is administered specifically to reach both the lower two thirds and the upper third of the nasal cavity.

Intranasal drug delivery has been a topic of research and development for many years, although it has been only within the past decade that carrier systems have been devised which make delivery of substances effective. (Sayani and Chien, *Critical Reviews in Therapeutic Drug Carrier Systems* 1996, 13:85-184.) Intranasal delivery has a number of advantageous features including comparatively high bioavailability, rapid kinetics of absorption and avoidance of a first-pass effect in the liver. In regard to patient compliance and ease of use, intranasal administration provides a simple, rapid and non-invasive mode of application. In some aspects, intranasal administration can allow for delivery of an analgesic peptide such as N/OFQ to the nasal cavity and in other aspects, intranasal administration can allow for targeted delivery to the cranial nerves of the nose and/or the brain. Without wishing to be bound by any particular theories, intranasal administration of an analgesic peptide such as N/OFQ can target either the olfactory nerve systems or the trigeminal nerve systems or both.

Like oral and intravenous delivery, intranasal delivery of peptides also has limitations of poor absorption and extensive hydrolysis if systemic circulation is required for the effect of the peptide administered. Enzyme inhibitors and absorption enhancers have been employed to increase the extent of peptide absorption. While nasal administration of leucine enkephalin, an opioid peptide, showed very limited analgesic effect in an acetic acid writhing test in mice (which models certain visceral pains), high analgesic activity was reported when leucine enkephalin was nasally administered with mixed enzyme inhibitors and absorption enhancers (Gawk H. S. et al., *Journal of Pharmacy and Pharmacology* 2003, 55:1207-1212.), an effect that may enhance both systemic absorption and targeted delivery to the cranial nerves and/or brain.

Within the oral cavity, the buccal or sublingual delivery routes are convenient choices for drug delivery as they are user-friendly and non-invasive. Some of the advantages include (i) less proteolytic activity in the oral cavity as compared to some other routes, thereby avoiding the problems of enzymatic degradation of peptide and protein drugs, and (ii) bypassing the hepatic first pass effect. Drug delivery to the mucosal tissue around the eye or to the conjunctiva is another convenient choice for drug delivery that is non-invasive.

Some aspects of the present invention include methods for treatment of pain such as headache pain or trigeminal neuralgia pain in an individual comprising administering an effective amount of an analgesic peptide such as N/OFQ to the conjunctiva or other mucosal tissues around the eye.

Transdermal drug delivery or administration of a therapeutic agent to the skin has become a proven technology over the last 20 years. Transdermal drug delivery offers controlled release of a drug to the patient and transdermal patches are user-friendly, convenient, painless, and offer multi-day dosing which usually results in improved patient compliance. The methods can include administering an analgesic compound (e.g. a non-opioid analgesic peptide, an NOP agonist or N/OFQ) or a pharmaceutical composition comprising an analgesic compound (e.g. a non-opioid analgesic peptide, an NOP agonist or N/OFQ) to skin of the face, head or body. An NOP agonist can be administered to the skin of the face, scalp or temporal region. Suitable skin of the face includes skin of the chin, upper lip, lower lip, forehead, nose, cheek, skin around the eyes, upper eyelid, lower eyelid or combinations thereof. Suitable skin of the scalp includes the front of the scalp, the scalp over the temporal region, the lateral part of the scalp, or combinations thereof. Suitable skin of the temporal region includes the temple and the scalp over the temporal region and combinations thereof.

Intradermal administration of a therapeutic agent is defined as within or between the layers of skin. In contrast, subcutaneous administration is defined as beneath the initial layer of skin. Administrations of therapeutic agents by intradermal or subcutaneous injection are common means of drug delivery by one skilled in the art.

In some embodiments, craniofacial mucosal administration of an analgesic compound (e.g. a non-opioid analgesic peptide, an NOP agonist or N/OFQ) or a pharmaceutical composition comprising an analgesic compound (e.g. a non-opioid analgesic peptide, an NOP agonist or N/OFQ) results in prevention or alleviation of pain without numbness as compared to local anesthetics or the strong sedative effect associated with narcotic type drugs. Targeted delivery can decrease the amount of the analgesic compound administered to an individual to achieve an analgesic effect, and can decrease potential undesirable CNS effects or systemic side effects.

In one aspect, provided herein is a method for treatment of migraine in an individual comprising administering to the individual an analgesic compound (e.g. a non-opioid analgesic peptide, an NOP agonist or N/OFQ) or a pharmaceutical composition comprising an analgesic compound (e.g. a non-opioid analgesic peptide, an NOP agonist or N/OFQ) through a craniofacial mucosal route. In some embodiments, the craniofacial mucosal route is a nasal, a conjunctival, a sublingual or a buccal route. In some embodiments, the method comprises treatment of migraine headache. In some embodiments, the method comprises treatment of migraine without aura. In some embodiments, the method comprises treatment of migraine with aura. In some embodiments, the method comprises treatment of migraine with aura but without headache. In some embodiments, the method comprises treatment of basilar type migraine. In some embodiments, the method comprises treatment of familial hemiplegic migraine or sporadic hemiplegic migraine. In some embodiments, the method comprises, treatment of abdominal migraine. In some embodiments, the method comprises treatment of acephalgic migraine. In some embodiments, the method comprises treatment of menstrual migraine. In a particular embodiment, the method for treating migraine comprises administering to an individual in need thereof an effective dose of N/OFQ or a pharmaceutical composition comprising N/OFQ via intranasal administration.

In another aspect, provided is a method for treatment of a symptom associated with migraine in an individual comprising administering to the individual an analgesic compound (e.g. a non-opioid analgesic peptide, an NOP agonist or N/OFQ) or a pharmaceutical composition comprising an analgesic compound (e.g. a non-opioid analgesic peptide, an NOP agonist or N/OFQ) via craniofacial mucosal administration (e.g. intranasal administration, buccal administration, sublingual administration or conjunctival administration). In some embodiments, the symptom is a prodrome phase symptom. In some embodiments, the symptom is an aura phase symptom. In some embodiments, the symptom is a pain phase symptom. In some embodiments, the symptom is a postdrome phase symptom. In some embodiment, the method comprises alleviating or preventing one or more migraine-associated symptoms selected from nausea, photophobia and phonophobia. In a particular embodiment, the method comprises administering to an individual in need thereof an effective dose of N/OFQ or a pharmaceutical composition comprising N/OFQ via intranasal administration, wherein the administration alleviates or prevents a symptom associated with migraine such as nausea, photophobia or phonophobia.

In some aspects, the invention provides methods for the treatment of pain by craniofacial mucosal administration (e.g. intranasal administration, buccal administration, sublingual administration or conjunctival administration) of an analgesic compound (e.g. a non-opioid analgesic peptide, an NOP agonist or N/OFQ). In some embodiments, the pain is a somatic pain. In some embodiments, the pain is a superficial somatic pain. In some embodiments, the pain is a deep somatic pain. In some embodiments, the pain is a musculoskeletal pain. In some embodiments, the pain is a visceral pain. In some embodiments, the pain is a neuropathic pain. In some embodiments, the pain is a head pain or a craniofacial pain. In some embodiments, the pain is in parts of the body other than the head and/or orofacial region. In some embodiments, the pain is a chronic pain such as a chronic pain described herein. In some embodiments, the pain is an acute pain such as an acute pain described herein. In some embodiments, the pain is a combination of one or more of the pain described herein. In some embodiment, the pain is a sharp and shooting pain associated with movement. In some embodiments, the pain is a neuropathic pain is caused by surgery related nerve injury.

Co-Administration

In some aspects of the invention a vasoconstrictor is used to decrease systemic uptake of an analgesic compound (e.g. a non-opioid analgesic peptide, an NOP agonist or N/OFQ). The vasoconstrictor can be included in a pharmaceutical composition to decrease systemic uptake of the analgesic compound. Alternatively, the vasoconstrictor may be delivered to the mucosal or dermal surface separately from the pharmaceutical composition. Vasoconstrictors are compounds that constrict blood vessels and capillaries and decrease blood flow. They can be used to increase concentration of an agent at a desired site by inhibiting movement of the agent into the bloodstream and thereby reducing systemic uptake and distribution of the agent. Vasoconstrictors can be used to decrease the effective dosage of an agent needed to achieve analgesia by limiting systemic distribution and concentrating the agent in targeted tissues, i.e. the cranial nerves and CNS. Accordingly, a vasoconstrictor can be administered before administration of an analgesic peptide or can be co-administered with an analgesic peptide. Vasoconstrictors may include, but are not limited to, phenylephrine hydrochloride, tetrahydrozoline hydrochloride, naphazoline nitrate, oxymetazoline hydrochloride, tramazoline hydrochloride, ergotamine, dihydroergotamine, endothelin-1, endothelin-2, epinephrine, norepinephrine and angiotensin.

In some embodiments, provided are methods wherein a vasoconstrictor is administered to the nasal cavity of an individual prior to administration of an analgesic compound (e.g. a non-opioid analgesic peptide, an NOP agonist or N/OFQ), wherein administration of the vasoconstrictor decreases systemic distribution of the analgesic compound. In some examples, the methods can co-administer a vasoconstrictor and an analgesic compound to the nasal cavity of an individual, wherein administration of the vasoconstrictor decreases systemic distribution of the analgesic compound. In other examples, the methods can administer a vasoconstrictor to the nasal cavity of an individual prior to or co-administer with an analgesic compound, wherein administration of the vasoconstrictor decreases systemic uptake and distribution of the analgesic compound, thereby decreasing the effective dosage requirement of the analgesic compound necessary to achieve analgesia.

In some aspects, provided herein are methods for treating an individual for pain, comprising: administering to the individual an effective amount of an analgesic compound (e.g. a non-opioid analgesic peptide, an NOP agonist or N/OFQ) or a pharmaceutical composition comprising an analgesic compound (e.g. a non-opioid analgesic peptide, an NOP agonist or N/OFQ) through a craniofacial mucosal route, wherein the analgesic compound is administered in combination with at least one additional active agent. In some embodiments, the analgesic compound (e.g. a non-opioid analgesic peptide, an NOP agonist or N/OFQ) is administered in combination with at least two additional active agents. Additional active agents may include, but are not limited to, non-peptide opioids, such as morphine, methadone, fentanyl, butorphanol, codeine, opium, oxycodone, loperimide, meperidine (Demerol®), diphenoxylate, propoxyphene (Darvon®), 4-methyl fentanyl, hydrocodone, morphine, diacetylmorphine, dihydrocodeine, hydromorphone (Dilaudid®), levorphanol (Levo-Dromoran®), dextromethorphan, oxymorphone (Numorphan®), heroin, remifentanil, phenazocine, pentazocine, piminodine, anileridine, buprenorphine (Suboxone®), sufentanil, carfentanil, alfentanil and the atypical opiates, tramadol and tapentadol; opioid and opioid-like peptides and their analogs, such as endorphins, enkephalins, dynorphins, dermorphins, dermenkephalins, morphiceptin, endomorphins and dalargin; NMDA-receptor antagonists, such as ketamine, amantadine, dextrometorphane, memantine and MK801; sodium channel blockers, such as local anesthetics and ergotamine; calcium channel blockers, such as verapamil and nifedipine; adrenergic antagonists, such as propranolol, metoprolol and yohimine; gabaergic agonists, such as GABA, baclofen, cis-4-aminocrotonic acid (CACA), trans-4-aminocrotonic acid (TACA), CGP 27 492 (3-aminopropyl phosphonous acid) and progabide; glycine agonists, such as glycine and D-cycloserine; cholinergic agonists, such as neostigmine and physiostigmine; adrenergic agonists, such as epinephrine, neosynephrine, clonidine and dexmedetomidine; anticonvulsants, such as gabapentin and barbiturates; Rho kinase inhibitors, such as fasudil, Y27632, H-1152 and derivatives thereof; PKC inhibitors, such as chelerythrine, Go 6983, Go 6976, N-myristoyl-Ser-Ile-Tyr-Arg-Arg-Gly-Ala-Arg-Arg-Trp-Arg-Lys-Leu, Rottlerin, KAI-9803 and KAI-1455; p38-MAP kinase inhibitors, such as SCIO-469, AMG548 and derivatives thereof; ATP receptor blockers, such as tetramethylpyrazine chelerythrine chloride, A-317491 and derivatives thereof; endothelin receptor blockers, such as BQ123, BMS182874 and derivatives thereof; pro-inflammatory cytokine, chemokine, interleukin and tumor necrosis factor blockers, such as anakinra, infliximab, etanercept and adalimumab; anti-inflammatory cytokines, such as interleukin-4, interleukin-10 and interleukin-13; tricyclic antidepressants, such as desipramine and amitryptiline; serotonergic antagonists, such as fluoxetine, dolasetron and ondansetron; serotonergic agonists, such as buspirone and ergometrine;

NSAIDs and COXIBs, such as diclofenac, ibuprofen, ketorolac, salicylate, rofecoxib, celecoxib, parecoxib, valdecoxib and naproxen; acetaminophen; analgesic peptides, such as calcitonin, octreotide, somatostatin, vasopressin, galanin, the C-fragment of lipotropin and Ac-rfwink-$NH_2$; toxins, such as botulinum toxin, variants and derivatives thereof, cone snail toxins, such as omega-conotoxin GV1A, omega-conotoxin MVIIA, saxitoxin and tetrodotoxin; TRP channel agonists and antagonists, such as capsaicin, capsazepine, resiniferotoxin, SB-705498, A-425619, AMG 517, SC0030 and derivatives thereof; cannabanoids, such as THC, CT-3, levonantradol, dexanabinol, WIN-55,212-2, AM 1241, dronabinol, nabilone, cannabis medicinal extract (CME) and derivatives thereof; antagonists of pro-nociceptive peptide neurotransmitter receptors CGRP1 and CGRP2, including non-peptide antagonists such as BIBN4096 and derivatives thereof and peptide antagonists such as CGRP 8-37 and CGRP 28-3; antagonists of pro-nociceptive peptide neurotransmitter receptor NK1, including non-peptide antagonists such as SR140333, CP96346, L-760735; RP 67580, WIN 51708; MK869, and derivatives thereof and peptide antagonists such as N-acetyl tryptophan, D-Pro9-[Spiro-y-lactam]-Leu 10,Trp 11-Physalaemin(1-11), Tyr-D-Phe-Phe-D-His-Leu-Met-$NH_2$ (Sendide) and spantide II; antagonists of pro-nociceptive peptide neurotransmitter receptor NK2, including non-peptide antagonists such as SR 48968 and derivatives thereof and peptide antagonists such as PhCO-Ala-Ala-D-Trp-Phe-D-Pro-Pro-Nle-$NH_2$ (GR98400), [Tyr5,D-Trp6,8,9,Lys10]-NKA (4-10) (MEN10376) and derivatives thereof; antagonists of pro-nociceptive peptide neurotransmitter receptor Y1-5, including non-peptide antagonist benextramine and peptide antagonists (Ile-Glue-Pro-Dpr-Tyr-Arg-Leu-Arg-Tyr-$NH_2)_2$, cyclic (2,4'),(2,4')-diamide (1229U91 or GW1229), PYX-2, D-Tyr (27,36), D-Thr (32)] NPY (27-36) (D-NPY(27-36), 3-(5,6,7,8-tetrahydro-9-isopropyl-carbazol-3-yl)-1-methyl-1-(2-pyridin-4-yl-ethyl)urea hydrochloride (FMS586 and derivatives thereof); antagonists of pro-nociceptive peptide neurotransmitter receptors VPAC2, VPAC1 and PAC1, including peptide antagonists VIP(6-28), Ac His(1) [D-Phe(2), K(15), R(16), L(27)] VIP (3-7)/GRF (8-27); antagonists of pro-nociceptive neurotransmitter receptors Gal1-3 and GalR1-3, including non-peptide antagonists SNAP 37889, SNAP 398299, galnon and derivatives thereof. Additional active agents may include agonists or antagonists of vasopressin, corticotropin releasing hormone (CRH), growth hormone releasing hormone (GHRH), luteinizing hormone releasing hormone (LHRH), somatostatin growth hormone release inhibiting hormone, thyrotropin releasing hormone (TRH), glial-derived neurotrophic factor (GDNF), brain-derived neurotrophic factor (BDNF), nerve growth factor (NGF), neurotrophin-3 (NT-3), pancreatic polypeptide, peptide tyrosine-tyrosine, glucogen-like peptide-1 (GLP-1), peptide histidine isoleucine (PHI), pituitary adenylate cyclase activating peptide (PACAP), brain natriuretic peptide, cholecystokinin (CCK), islet amyloid polypeptide (IAPP) or amylin, melanin concentrating hormone (MCH), melanocortins (ACTH, .alpha.-MSH and others), neuropeptide FF (F8Fa), neurotensin, parathyroid hormone related protein, Agouti gene-related protein (AGRP), cocaine and amphetamine regulated transcript (CART)/peptide, 5-HT-moduline, hypocretins/orexins, an oxytocin peptide, nocistatin, prolactin releasing peptide, secretoneurin, urocortin and derivatives and analogues thereof.

Pharmaceutical Compositions

While it is possible to administer an analgesic compound (e.g. a non-opioid analgesic peptide, an NOP agonist or N/OFQ) alone, there are situations wherein it is advantageous to present it as part of a pharmaceutical composition. Thus, in some aspects of the present invention, an analgesic compound (e.g. a non-opioid analgesic peptide, an NOP agonist or N/OFQ) is administered as a pharmaceutical composition. The pharmaceutical composition can comprise an analgesic compound (e.g. a non-opioid analgesic peptide, an NOP agonist or N/OFQ) at a therapeutically effective dose together with one or more pharmaceutically acceptable carriers and optionally other ingredients. A suitable carrier is one which does not cause an intolerable side effect, but which allows an analgesic compound (e.g. a non-opioid analgesic peptide, an NOP agonist or N/OFQ) to retain its pharmacological activity in the body. A carrier may also reduce any undesirable side effects of the analgesic compound. A suitable carrier should be stable, i.e., not typically reacting with other ingredients in the formulation. A suitable carrier should have minimal undesirable odor or fragrance, but could include a desirable fragrance or a positive (pleasant) odor. A suitable carrier should not irritate the mucosa, epithelium, underlying nerves or provide a health risk.

Suitable nontoxic pharmaceutically acceptable carriers will be apparent to those skilled in the art of pharmaceutical formulations. Also see Remington: The Science and Practice of Pharmacy, 20th Edition, Lippincott, Williams & Wilkins (2000). Typical pharmaceutically acceptable carriers include, but are not limited to, mannitol, urea, dextrans, lactose, potato and maize starches, magnesium stearate, talc, vegetable oils, polyalkylene glycols, ethyl cellulose, poly(vinylpyrrolidone), calcium carbonate, chitosan, ethyl oleate, isopropyl myristate, benzyl benzoate, sodium carbonate, gelatin, potassium carbonate, silicic acid, and other conventionally employed acceptable carriers. Other carriers include, but are not limited to, phosphatidylcholine, phosphatidylserine, and sphingomyelins.

The choice of a suitable carrier will depend on the exact nature of the particular formulation desired, e.g., whether the drug is to be formulated into a liquid solution (e.g., for use as drops, for use in an injection, as a spray or impregnated in a nasal tampon, or other agent-impregnated solid), a suspension, an ointment, a film or a gel. If desired, sustained-release compositions, e.g. sustained-release gels, films, transdermal patches, etc. can be readily prepared. The particular formulation will also depend on the route of administration. The agent can be administered to the nasal cavity as a powder, a granule, a solution, a cream, a spray, a gel, a film, an ointment, an infusion, a drop or a sustained-release composition. For buccal administration, the composition can take the form of tablets or lozenges formulated in a convention manner. For sublingual administration, the composition can take the form of a bioadhesive, a spray, a powder, paint or a swab applied to or under the tongue. For administration to the conjunctiva or other mucosal tissues around the eye, the composition can be applied as an ointment, a solution or a drop. For administration to the skin, the composition can be applied as a topical ointment, a topical gel, a lotion, a cream, a solution, a spray, a paint, a film, a foil, a cosmetic, a patch or a bioadhesive.

Liquid carriers include, but are not limited to, water, saline, aqueous dextrose, and glycols particularly (when isotonic) for solutions. The carrier can also be selected from various oils, including those of petroleum, animal, vegetable or synthetic origin, (e.g. peanut oil, soybean oil, mineral oil, sesame oil, and the like). Suitable pharmaceutical excipients include, but are not limited to, starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions can be subjected to conventional pharmaceutical processes, such as sterilization, and can contain conventional pharmaceutical additives, such as preservatives, stabilizing agents, reducing agents, antioxidants, chelating agents, wetting agents, emulsifying agents, dispersing agents, jelling agents, salts for adjusting osmotic pressure, buffers, and the like. Where the carrier is a liquid, the carrier may be hypotonic or isotonic with body fluids and may have a pH within the range of 4.5-8.5. Where the carrier is in powdered form, it is preferred that the carrier be within an acceptable non-toxic pH range. The use of additives in the preparation of peptide and/or protein-based compositions, particularly pharmaceutical compositions, is well-known in the art.

The lists of carriers and additives discussed herein are by no means complete and a worker skilled in the art can choose carriers and excipients from the GRAS (generally regarded as safe) list of chemicals allowed in pharmaceutical preparations and those that are currently allowed in topical and parenteral formulations. (See also Wang et al., (1980) *J. Parent. Drug Assn.*, 34:452-462; Wang et al., (1988) *J. Parent. Sci. and Tech.*, 42:S4-S26.)

Other forms of compositions for administration include a suspension of a particulate, such as an emulsion, a liposome, or in a sustained-release form to prolong the presence of the pharmaceutically active agent in an individual. The powder or granular forms of the pharmaceutical composition may be combined with a solution and with a diluting, dispersing or surface-active agent. Additional compositions for administration include a bioadhesive to retain the agent at the site of administration, for example a spray, paint, or swab applied to the mucosa or epithelium. A bioadhesive can refer to hydrophilic polymers, natural or synthetic, which, by the hydrophilic designation, can be either water soluble or swellable and which are compatible with the pharmaceutical composition. Such adhesives function for adhering the formulations to the mucosal tissues of the oral or nasal cavity. Such adhesives can include, but are not limited to, hydroxypropyl cellulose, hydroxypropyl methylcellulose, hydroxy ethylcellulose, ethylcellulose, carboxymethyl cellulose, dextran, gaur gum, polyvinyl pyrrolidone, pectins, starches, gelatin, casein, acrylic acid polymers, polymers of acrylic acid esters, acrylic acid copolymers, vinyl polymers, vinyl copolymers, polymers of vinyl alcohols, alkoxy polymers, polyethylene oxide polymers, polyethers, and combinations thereof. The composition can also be in the form of lyophilized powder, which can be converted into solution, suspension, or emulsion before administration. The pharmaceutical composition is preferably sterilized by membrane filtration and is stored in unit-dose or multi-dose containers such as sealed vials or ampoules.

The pharmaceutical composition can be formulated in a sustained-release form to prolong the presence of the active agent in the treated individual. Many methods of preparation of a sustained-release formulation are known in the art and are disclosed in Remington's Pharmaceutical Sciences (see above). Generally, the agent can be entrapped in semi-permeable matrices of solid hydrophobic polymers. The matrices can be shaped into films or microcapsules. Matrices can include, but are not limited to, polyesters, co-polymers of L-glutamic acid and gamma ethyl-L-glutamate, polylactides, polylactate polyglycolate, hydrogels, non-degradable ethylene-vinyl acetate, degradable lactic acid-glycolic acid copolymers, hyaluronic acid gels, and alginic acid suspensions. Suitable microcapsules can also include hydroxymethylcellulose or gelatin and poly-methyl methacrylate. Microemulsions or colloidal drug delivery systems such as liposomes and albumin microspheres can also be used. Some sustained-release compositions can use a bioadhesive to retain the agent at the site of administration.

To further enhance the mucosal delivery of a pharmaceutical composition comprising an analgesic compound (e.g. a non-opioid analgesic peptide, an NOP agonist or N/OFQ), an enzyme inhibitor, particularly proteases inhibitors, can be included in the formulation. Protease inhibitors may include, but are limited to, antipain, arphamenine A and B, benzamidine HCl, AEBSF, CA-074, calpain inhibitor I and II, calpeptin, pepstatin A, actinonin, amastatin, bestatin, boroleucine, captopril, chloroacetyl-HOLeu-Ala-Gly-NH2, DAPT, diprotin A and B, ebelactone A and B, foroxymithine, leupeptin, pepstatin A, phosphoramidon, aprotinin, puromycin, BBI, soybean trypsin inhibitor, phenylmethylsulfonyl fluoride, E-64, chymostatin, 1,10-phenanthroline, EDTA and EGTA.

To enhance delivery into or across a mucosal surface and/or absorption of a pharmaceutical composition comprising an analgesic compound (e.g. a non-opioid analgesic peptide, an NOP agonist or N/OFQ), an absorption-enhancing agent can be included in the formulation. These enhancing agents may enhance the release or solubility (e.g., from a formulation delivery vehicle), diffusion rate, penetration capacity and timing, uptake, residence time, stability, effective half-life, peak or sustained concentration levels, clearance and other desired mucosal delivery, characteristics (e.g., as measured at the site of delivery) of the composition. Enhancement of mucosal delivery can thus occur by any of a variety of mechanisms, for example by increasing the diffusion, transport, persistence or stability of an analgesic compound (e.g. a non-opioid analgesic peptide, an NOP agonist or N/OFQ), increasing membrane fluidity, modulating the availability or action of calcium and other ions that regulate intracellular or paracellular permeation, solubilizing mucosal membrane components (e.g., lipids), changing non-protein and protein sulfhydryl levels in mucosal tissues, increasing water flux across the mucosal surface, modulating epithelial junctional physiology, reducing the viscosity of mucus overlying the mucosal epithelium, reducing mucociliary clearance rates, and other mechanisms.

Mucosal absorption enhancing compounds may include, but are not limited to, surfactants, bile salts, dihydrofusidates, bioadhesive agents, phospholipid additives, mixed micelles, liposomes, or carriers, alcohols, enamines, cationic polymers, NO donor compounds, long-chain amphipathic molecules, small hydrophobic penetration enhancers; sodium or a salicylic acid derivatives, glycerol esters of acetoacetic, acid, cyclodextrin or beta-cyclodextrin derivatives, medium-chain fatty acids, chelating agents, amino acids or salts thereof, N-acetylamino acids or salts thereof, mucolytic agents, enzymes specifically targeted to a selected membrane component, inhibitors of fatty acid synthesis and inhibitors of cholesterol synthesis.

These additional agents and compounds can be coordinately administered or combinatorially formulated with an analgesic compound (e.g. a non-opioid analgesic peptide, an NOP agonist or N/OFQ). Accordingly, some aspects of the present invention include methods wherein an analgesic compound (e.g. a non-opioid analgesic peptide, an NOP agonist or N/OFQ) is administered as a pharmaceutical composition that comprises protease inhibitors, absorption enhancers, vasoconstrictors or combinations thereof. The pharmaceutical composition can be administered to the nasal cavity, oral cavity, to conjunctiva or other mucosal tissues around the eye or to the skin. The pharmaceutical composition can be administered by an intranasal route. The pharmaceutical composition can be administered by a buccal or sublingual route. The pharmaceutical composition can be administered by a transdermal route. The pharmaceutical composition can be administered by more than one route. The pharmaceutical composition can include at least one protease inhibitor, at least one absorption enhancer, at least one vasoconstrictor or combinations thereof. The pharmaceutical composition can be co-administered with a vasoconstrictor or administered after the vasoconstrictor has been delivered.

Dosages

An analgesic compound (e.g. a non-opioid analgesic peptide, an NOP agonist or N/OFQ) is administered in a dose sufficient to provide a therapeutically effective amount to an individual suffering from pain. In some aspects, an analgesic compound (e.g. a non-opioid analgesic peptide, an NOP agonist or N/OFQ) can be administered via a craniofacial mucosal route (e.g. intranasal route) in a dose that results in a global analgesic effect with minimal CNS or systemic side effects. A therapeutically effective dose of an analgesic compound (e.g. a non-opioid analgesic peptide, an NOP agonist or N/OFQ) can be determined empirically and depends on the type and severity of the pain, the route of administration, and the size, weight, age and overall health of the patient, as is within the skill of one in the art such as a medical practitioner.

The amount of an analgesic compound (e.g. a non-opioid analgesic peptide, an NOP agonist or N/OFQ) administered as a unit dose will depend upon the type of pharmaceutical composition being administered, for example, a solution, a suspension, a gel, a film, an emulsion, a powder, or a sustained-release formulation. In some examples, the effective dosage will be lower than dose amounts needed for oral, intravenous, intramuscular or subcutaneous administration, since transmucosal or transdermal delivery may allow for a more concentrated level of the analgesic compound within the craniofacial and head region. The quantity of formulation needed to deliver the desired dose will also depend on the concentration of the analgesic compound in the composition. Such determinations are within the skill of one in the art.

The therapeutic dosage of an analgesic compound (e.g. a non-opioid analgesic peptide, an NOP agonist or N/OFQ) in the pharmaceutical compositions used in the methods of the present invention will depend on a number of factors such as the chemical composition and/or modification of the analgesic compound, its bioavailability by the chosen route of administration, its efficacy, the desired frequency of administration combined with the desired single dosage of the formulation and whether the analgesic compound is administered in combination with other active agent(s). Particularly, the dosage of an analgesic compound (e.g. a non-opioid analgesic peptide, an NOP agonist or N/OFQ) will be chosen to maximize alleviation of the particular pain to be treated. Pharmacological data can be obtained from animal models and clinical trials with normal human volunteers or patients experiencing a particular pain by one with skill in the art.

Experimental models to test for analgesic activity of agents are known in the art. Animal models comprise tests which include, but are not limited to, acetic acid writhing, phenylquinone writhing, tail-flick, paw withdrawal and cheek/ear/face withdrawal wherein the pain receptor activation is induced by such compounds as acetic acid, phenylquinone, formalin or capsaicin, or by thermal activators such as a hot plate or a laser. In particular, models for craniofacial or head pain utilizing tests such as orofacial delivery of capsaicin, orofacial delivery of formalin, or delivery of thermal heat to the cheek, ear or the face are available. In some instances, other models can be developed to test for analgesic activities, such as the models described in the Examples described herein. Models can be used to determine optimal dosage ranges wherein an analgesic agent results in a desired analgesic effect with minimal CNS and/or systemic side effect. Further, models can be used to administer an analgesic compound by a particular delivery route, e.g. intranasally, and test for analgesic effect at the cheeks, ears or the face and at the hindpaws. In some instances, one model can be used to test for analgesic activity of an analgesic agent after administration of a pharmaceutical composition wherein withdrawal latencies at the cheek, ear or face can determine regional analgesia while withdrawal latencies at the hindpaw can determine the global analgesic effect.

As stated above, an effective amount of an analgesic compound (e.g. a non-opioid analgesic peptide, an NOP agonist or N/OFQ) will depend on the form and composition being used in the method. Preferably the effective amount of an N/OFQ peptide administered via craniofacial mucosal administration is lower than dosages used when the agent is delivered by other routes (e.g. oral, intravenous, intramuscular or subcutaneous) which may not achieve an effect at all, or only at very high doses. For example, dosages used for administration of an N/OFQ peptide can include, but are not limited to, an effective amount within the dosage range of about 0.2 mg to about 5000 mg, about 0.2 mg to about 2000 mg, about 0.2 mg to about 1000 mg, about 0.2 mg to about 500 mg, about 0.2 mg to about 200 mg, or 0.2 mg to about 100 mg, or 0.5 mg to about 100 mg, or about 0.5 mg to about 50 mg, or about 0.5 mg to about 25 mg, or about 0.5 mg to about 10 mg, or about 0.5 mg to about 5 mg, or about 0.5 mg to about 1 mg, or about 1 mg to about 100 mg, or about 1 mg to about 50 mg, or about 1 mg to about 25 mg, or about 1 mg to about 10 mg, or about 1 mg to about 5 mg, or about 5 mg to about 200 mg, or 5 mg to about 100 mg, or about 5 mg to about 50 mg, or about 5 mg to about 25 mg, or about 5 mg to about 10 mg.

Dosages can be administered in a single dose or in multiple doses, for example, dosages can be administered two, three, four, up to ten times daily depending on the type and severity of headache pain being treated as well as on individual susceptibility. Dosages can be administered in a sustained release formulation which may allow for an N/OFQ peptide to be administered less frequently such as six times a week, five times a week, four times a week, three times a week, twice a week, or once a week.

Thus some aspects of the present invention include methods for treatment of pain comprising administering to an individual an effective amount of an N/OFQ peptide via intranasal administration. The N/OFQ peptide can be administered within a dosage range determined by methods known in the art such as studies in animal models and/or human clinical trials. For examples, the unit dose can be in the range of about 0.2 mg to about 5000 mg, about 0.2 mg to about 2000 mg, about 0.2 mg to about 1000 mg, about 0.2 mg to about 500 mg, about 0.2 mg to about 200 mg, or 0.2 mg to about 100 mg, or 0.5 mg to about 100 mg, or about 0.5 mg to about 50 mg, or about 0.5 mg to about 25 mg, or about 0.5 mg to about 10 mg, or about 0.5 mg to about 5 mg, or about 0.5 mg to about 1 mg, or about 1 mg to about 100 mg, or about 1 mg to about 50 mg, or about 1 mg to about 25 mg, or about 1 mg to about 10 mg, or about 1 mg to about 5 mg, or about 5 mg to about 200 mg, or 5 mg to about 100 mg, or about 5 mg to about 50 mg, or about 5 mg to about 25 mg, or about 5 mg to about 10 mg.

In some aspects of the present invention, a composition comprising an analgesic compound (e.g. a non-opioid analgesic peptide, an NOP agonist or N/OFQ) may further comprise an additional active agent, wherein the analgesic compound and the additional active agent(s) are administered as a mixture, separately and simultaneously, or separately in any order. In some examples the composition comprising an N/OFQ peptide is administered in combination with at least one additional active agent. In other examples, the composition comprising an N/OFQ peptide is administered in combination with at least two additional active agents. In other examples, the composition comprises an N/OFQ peptide administered in combination with diclofenac, oxytocin or an oxytocin antagonist.

To determine the therapeutic effect of an analgesic compound (e.g. a non-opioid analgesic peptide, an NOP agonist or N/OFQ) or a composition comprising an analgesic compound (e.g. a non-opioid analgesic peptide, an NOP agonist or N/OFQ), the "visual analogue scale" (VAS) may be used to assess the reduction or alleviation of pain after administration of the analgesic compound. VAS is a 10 cm horizontal or vertical line with word anchors at each end, such as "no pain" and "pain as bad as it could be". A subject or patient is asked to make a mark on the line to represent pain intensity. This mark is converted to distance in either centimeters or millimeters from the "no pain" anchor to give a pain score that can range from 0-10 cm or 0-100 mm. The VAS is similar to an 11 point numerical pain rating scale wherein 0 equals "no pain" and 10 equals the "worst pain imaginable," and can alternatively be used. Using the VAS, an analgesic compound, e.g. a non-opioid analgesic peptide, an NOP agonist or an N/OFQ peptide, is considered to have a particularly relevant clinical analgesic effect when there is a change of about 30% or more, for example a change from 9 to 7 or from 5 to 3.5.

Delivery Systems

An analgesic compound (e.g. a non-opioid analgesic peptide, an NOP agonist or N/OFQ) or a pharmaceutical composition comprising an analgesic compound (e.g. a non-opioid analgesic peptide, an NOP agonist or N/OFQ) may be dispensed to the buccal or sublingual surfaces in a number of different formulations or dosage forms including, but not limited to, fast-melting tablets, liquid-filled capsules, liquid sprays or lozenges. Alternatively, a pharmaceutical composition can be delivered to the mucosa of the oral cavity by direct placement of the composition in the mouth, for example, with a gel, a film, an ointment, a dropper, or a bioadhesive strip or patch.

In some aspects of the present invention, the methods comprise administering to an individual a pharmaceutical composition wherein administration to the buccal and/or sublingual mucosal surfaces of the oral cavity is by a delivery device. The delivery device can include, but is not limited to unit dose containers, pump sprays, droppers, squeeze bottles, airless and preservative-free sprays, nebulizers, dose inhalers and pressurized dose inhalers. The delivery device can be metered to administer an accurate effective dosage amount (as described below) to the oral cavity. In some aspects, an accurate effective dosage amount is contained within a capsule, tablet, lozenge, or bioadhesive patch that is placed directly within the oral cavity.

An analgesic compound (e.g. a non-opioid analgesic peptide, an NOP agonist or N/OFQ) or a pharmaceutical composition comprising an analgesic compound (e.g. a non-opioid analgesic peptide, an NOP agonist or N/OFQ) may be dispensed to the conjunctiva or to other mucosal tissues around the eye in a number of different formulations such as a liquid drop, a gel, a film, an ointment or a bioadhesive patch or strip. Thus, in some aspects of the present invention the methods comprise administering to an individual a pharmaceutical composition wherein administration is directed to the conjunctiva or other mucosal tissues around the eye. In some aspects, an accurate effective dosage amount is contained within a drop, a gel, a film, an ointment or a bioadhesive patch that is placed directly onto the mucosal tissues around the eye.

An analgesic compound (e.g. a non-opioid analgesic peptide, an NOP agonist or N/OFQ) or pharmaceutical composition comprising an analgesic compound (e.g. a non-opioid analgesic peptide, an NOP agonist or N/OFQ) may be administered to the skin or scalp in a number of different formulations such as a liquid, a spray, a gel, a film, an ointment or a bioadhesive patch or strip. Thus, in some aspects of the present invention the methods comprise administering to an individual a pharmaceutical composition wherein administration is directed to the skin of the face or scalp, e.g. anterior scalp skin. In some aspects, an accurate effective dosage amount is contained within a drop, a gel, a film, an ointment or a bioadhesive transdermal patch that is placed directly onto the skin. In some aspects, a pharmaceutical composition may be administered to the skin intradermally by injection. In other aspects the composition may be administered to the skin subcutaneously by injection.

An analgesic compound (e.g. a non-opioid analgesic peptide, an NOP agonist or N/OFQ) or a pharmaceutical composition comprising an analgesic compound (e.g. a non-opioid analgesic peptide, an NOP agonist or N/OFQ) may be dispensed intranasally as a powdered or liquid nasal spray, suspension, nose drops, a gel, film or ointment, through a tube or catheter, by syringe, by packtail, by pledget (a small flat absorbent pad), by nasal tampon or by submucosal infusion. Nasal drug delivery can be carried out using devices including, but not limited to, unit dose containers, pump sprays, droppers, squeeze bottles, airless and preservative-free sprays, nebulizers (devices used to change liquid medication to an aerosol particulate form), metered dose inhalers, and pressurized metered dose inhalers. It is important that the delivery device protect the drug from contamination and chemical degradation. The device should also avoid leaching or absorption as well as provide an appropriate environment for storage. Each drug needs to be evaluated to determine which nasal drug delivery system is most appropriate. Nasal drug delivery systems are known in the art and several are commercially available.

An analgesic compound (e.g. a non-opioid analgesic peptide, an NOP agonist or N/OFQ) or a pharmaceutical composition comprising an analgesic compound (e.g. a non-opioid analgesic peptide, an NOP agonist or N/OFQ) may be conveniently delivered in the form of an aerosol spray using a pressurized pack or a nebulizer and a suitable propellant including, but not limited to, dichlorodifluoromethane, trichlorofluoromethane, dichlorotetrafluoroethane, hydrocarbons, compressed air, nitrogen or carbon dioxide. An aerosol system requires the propellant to be inert towards the pharmaceutical composition. In the case of a pressurized aerosol, the dosage unit may be controlled by providing a valve to deliver an accurately metered amount.

The means to deliver an analgesic compound (e.g. a non-opioid analgesic peptide, an NOP agonist or N/OFQ) or a pharmaceutical composition comprising, an analgesic compound (e.g. a non-opioid analgesic peptide, an NOP agonist or N/OFQ) to the nasal cavity as a powder can be in a form such as microspheres delivered by a nasal insufflator device (a device to blow a gas, powder, or vapor into a cavity of the body) or pressurized aerosol canister. The insufflator produces a finely divided cloud of the dry powder or microspheres. The insufflator may be provided with means to ensure administration of a substantially metered amount of the pharmaceutical composition. The powder or microspheres should be administered in a dry, air-dispensable form. The powder or microspheres may be used directly with an insufflator which is provided with a bottle or container for the powder or microspheres. Alternatively the powder or microspheres may be filled into a capsule such as a gelatin capsule, or other single dose device adapted for nasal administration. The insufflator can have means such as a needle to break open the capsule or other device to provide holes through which jets of the powdery composition can be delivered to the nasal cavity.

Nasal delivery devices can be constructed or modified to dispense an analgesic compound (e.g. a non-opioid analgesic peptide, an NOP agonist or N/OFQ) or a pharmaceutical composition comprising an analgesic compound (e.g. a non-opioid analgesic peptide, an NOP agonist or N/OFQ) wherein the analgesic compound or the composition is delivered predominantly to the inferior two-thirds of the nasal cavity. For example, the angle of dispersion from a delivery device such as a nebulizer or an insufflator can be set so that the pharmaceutical composition is mechanically directed to the inferior two-thirds of the nasal cavity, and away from the superior region of the nasal cavity. Alternatively, an analgesic compound (e.g. a non-opioid analgesic peptide, an NOP agonist or N/OFQ) or a pharmaceutical composition comprising an analgesic compound (e.g. a non-opioid analgesic peptide, an NOP agonist or N/OFQ) can be delivered to the inferior two-thirds of the nasal cavity by direct placement of the composition in the nasal cavity, for example, with a gel, an ointment, a nasal tampon, a dropper, or a bioadhesive strip. Alternatively, an analgesic compound (e.g. a non-opioid analgesic peptide, an NOP agonist or N/OFQ) or a pharmaceutical composition comprising an analgesic compound (e.g. a non-opioid analgesic peptide, an NOP agonist or N/OFQ) can be delivered to the superior region of the nose, or both the superior region and inferior region.

Thus in some aspects of the present invention, the methods comprise administering to an individual an analgesic compound (e.g. a non-opioid analgesic peptide, an NOP agonist or N/OFQ) or pharmaceutical composition comprising an analgesic compound (e.g. a non-opioid analgesic peptide, an NOP agonist or N/OFQ) wherein administration to the nasal cavity is by a nasal delivery device. The nasal delivery device can include, but is not limited to, unit dose containers, pump sprays, droppers, squeeze bottles, airless and preservative-free sprays, nebulizers, dose inhalers, pressurized dose inhalers, insufflators, and bi-directional devices. The nasal delivery device can be metered to administer an accurate effective dosage amount (as described below) to the nasal cavity. The nasal delivery device can be for single unit delivery or multiple unit delivery. In some embodiments, the nasal delivery device can be constructed whereby the angle of dispersion of a pharmaceutical composition is mechanically directed towards the inferior two-thirds of the nasal cavity thereby minimizing delivery to the olfactory region. In some embodiments, the nasal delivery device can be constructed whereby the angle of dispersion of a pharmaceutical composition is mechanically directed towards the superior region of the nose. In some embodiments, the nasal delivery device can be constructed whereby the angle of dispersion of a pharmaceutical composition is mechanically directed towards both the inferior and superior regions of the nose. In some embodiments, the nasal delivery device may be activated only on exhalation, thus limiting the inhalation induced and potentially undesirable distribution of the pharmaceutical composition. In some embodiments, the pharmaceutical composition is a gel, film, cream, ointment, impregnated in a nasal tampon or bioadhesive strip whereby the composition is placed in the inferior two-thirds of the nasal cavity, the superior region, or both. In some embodiments, the methods include intranasal administration of an analgesic compound (e.g. a non-opioid analgesic peptide, an NOP agonist or N/OFQ) or a pharmaceutical composition comprising an analgesic compound (e.g. a non-opioid analgesic peptide, an NOP agonist or N/OFQ) wherein the administration uses a nasal delivery device with an angle of dispersion that mechanically directs the agent to the inferior two-thirds of the nasal cavity wherein the analgesic compound is administered after a vasoconstrictor, or the superior region of the nose, or both the superior and inferior regions. In some embodiments, the methods include intranasal administration of an analgesic compound (e.g. a non-opioid analgesic peptide, an NOP agonist or N/OFQ) or pharmaceutical composition comprising an analgesic compound (e.g. a non-opioid analgesic peptide, an NOP agonist or N/OFQ) wherein the administration uses a nasal delivery device with an angle of dispersion that mechanically directs the agent to the inferior two-thirds, the superior region, or both the inferior and superior regions of the nasal cavity wherein the analgesic compound is co-administered with a vasoconstrictor.

Kits

Provided herein are kits for carrying out any of the methods described herein. Kits are provided for use in treatment and/or prevention of pain. In some embodiments, the kit comprises an analgesic compound (e.g. a non-opioid analgesic peptide, an NOP agonist or N/OFQ) in suitable packaging. In some embodiments, the kit comprises an N/OFQ peptide in suitable packaging. In some embodiments, the kit further comprises at least one additional analgesic agent. Kits may further comprise a vasoconstrictor, at least one protease inhibitor and/or at least one absorption enhancer. Some kits may further comprise a delivery device, including but not limited to, a device for intranasal administration. Other kits may further comprise instructions providing information to the user and/or health care provider for carrying out any one of the methods described herein.

Kits comprising a single component, for example an analgesic compound, e.g. a non-opioid analgesic peptide, an NOP agonist or an N/OFQ peptide, will generally have the component enclosed in a container (e.g., a vial, ampoule, or other suitable storage container). Likewise, kits including more than one component may also have the reagents in containers (separately or in a mixture).

The instructions relating to the use of the kit for carrying out the invention generally describe how the contents of the kit are used to carry out the methods of the invention. Instructions supplied in the kits of the invention are typically written instructions on a label or package insert (e.g., a paper sheet included in the kit), but machine-readable instructions (e.g., instructions carried on a magnetic or optical storage disk) are also acceptable.

EXAMPLES

The invention can be further understood by reference to the following examples, which are provided by way of illustration and are not meant to be limiting.

Example 1

One way to test activity of an analgesic compound in a rat model is by treatment-induced changes in latencies (times) of withdrawal in response to noxious heating of the skin, typically using an ear, the face or a hindpaw. Thus, application of coherent or non-coherent (non-laser) radiant heat to the ear, the face or hindpaw will elicit rapid withdrawal movements. Latencies of withdrawal have been demonstrated to be sensitive to analgesic treatments, such that analgesics increase the latency to withdrawal Transmucosal or transdermal administration of analgesic agents to the trigeminal nerve to reduce trigeminal nerve-associated pain can be tested for regional and/or global analgesic effects. The rostral external part of a rat's ear is innervated by a branch of the mandibular nerve, itself a branch of the trigeminal nerve. Thus after treatment, an increase in latency to withdrawal time would indicate regional analgesia. Similarly, a change in the latency to withdrawal time of the hindpaw would indicate a global analgesic effect.

Rats are housed in a 12/12-hour light/dark environment and are provided food and water ad libitum. Efforts are made to minimize discomfort and reduce the number of animals used Rats are lightly anesthetized with urethane and placed with minimal restraint on a heating pad to maintain their body temperature at 37° C. A laser beam is directed via a fiberoptic cable to the rostral external part of both ears. Characteristic responses to laser irradiation are a retraction or withdrawal of the stimulated ear for 1-3 seconds after a thermal stimulus by the laser. Laser stimulation is terminated rapidly after response of the stimulated ear or after a maximal response (cut-off) latency of 30 seconds to prevent tissue damage.

For baseline testing of latency withdrawal responses to the ear, 3 pulses are applied to the portion of each ear that is innervated by the trigeminal nerve. The stimulation site is changed after each pulse allowing at least 2 minutes in between 2 stimuli on the same ear. For baseline testing of latency withdrawal responses to the hindpaw, 3 pulses are applied to the hindpaw. The stimulation site is changed after each pulse allowing at least 2 minutes in between 2 stimuli on the same hindpaw. Testing sessions are videotaped for off-line analysis of responses. The off-line analysis is performed by an investigator who determines the latency of withdrawal responses to the laser stimulation and who is blinded to the treatment groups.

After measuring baseline latencies, analgesic agents are administered intranasally. This involves 5 equal 10 μl applications to the nose by pipette for a total volume of 50 μl over 20 minutes. The effect of different doses of an agent (e.g. 5 mg/kg N/OFQ) on latency responses is examined. To assess the local analgesic effect, the latency responses of the ear are tested at various time points after agent administration. To assess the systemic analgesic effect, the latency responses of hindpaws are tested at various time points after agent administration.

Example 2

Effect of Intranasal Nociceptin on Thermal Nociception

A thermal nociceptive rodent model was used to determine the dose response relationship of intranasal nociceptin to 1) latency withdrawal, 2) duration of effect, and 3) to provide evidence for or against the hypothesis that the analgesic effects of i.n. nociceptin are mediated centrally.

I. Equipment and Materials

Nine male Sprague-Dawley Rats (200-300 g) per test run, nociceptin in saline (i.n. concentrations: 0.5 mg/ml, 5.0 mg/ml, 50 mg/ml), i.v. nociceptin (50 mg/ml), morphine (1.25 mg/ml), saline, urethane, A-delta/C, algometer, timer.

II. Reference Documents

Yeomans, D. C. Pirec, V., and Proudfit, H. K. "Nociceptive responses to high or low rates of noxious cutaneous heating are mediated by different nociceptors in the rat: behavioral evidence" *Pain* (1996) 68:133-140.

Sherman S. E, Loomis C. W. "Morphine Insensitive Allodynia Is Produced By Intrathecal Strychnine in the Lightly Anesthetized Rat" *Pain* (1994) 56:17-29.

Thorne R. G., Pronk G. I, Padmanabhan V, Frey W. H. 2nd. "Delivery of Insulin-Like Growth Factor-I to the Rat Brain and Spinal Cord along Olfactory and Trigeminal Pathways following Intranasal Administration" *Neuroscience* (2004) 127:481-96.

III. Test Articles

Nociceptin in saline, morphine and saline.

IV. Test Matrix/Flowchart (A) Groups of six rats per test run were lightly anesthetized with urethane (1.0 g/kg, i.p., titrated to minimal activity in the absence of a stimulus) (Sherman and Loomis et al, 1996). The left and right cheeks and right hindpaw were blackened with India ink to allow even heat distribution.

(B) Each 200-300 g male Sprague-Dawley rat was subjected to varying heat intensities on the left and right check and right hindpaw for selective testing of A-delta vs. C fiber nociception (Yeomans et al., 1996).

For C-fiber testing, the heat intensity was adjusted by altering the supply voltage of a focused projector lamp until a withdrawal latency between 9-13 seconds was observed. The intensity applied (measured in volts) was noted for each animal. To reduce the potential for tissue damage, a cut-off latency of 20 seconds was used after which the stimulus was terminated. Rats not responding up to a supply voltage of 55 volts were excluded from the study.

For A-delta fiber testing, the heat intensity was adjusted until withdrawals occurred at latencies of between 2 and 3 seconds was observed. The intensity applied (measured in volts) was noted for each animal. To reduce potential tissue damage, a cut-off radiation time of 6 seconds was used Rats not responding up to a voltage of 85 volts were excluded from the study.

(C) Rats received one of the following:
48 μl intranasal (Frey Method, see below; Thorne et al., 2004) of saline or nociceptin (0.2, 1.0, and 5.0 mg/kg)
50 μl i.v. saline or nociceptin (5.0 mg/kg)
50 μl i.m. saline or morphine (0.25 mg/kg)

Experimenter was blinded as to the nature of substance given.

(D) Withdrawal latencies were measured in response to radiant heat stimulation of the left and right cheeks, followed by similar measurements of response latencies for each hindpaw. Each animal was tested using its specific radiant amplitude (volts) established in baseline testing. Measurements were taken immediately after dosing and at 15, 30, 45, 60, 90, 120, 150, and 180 min after dosing.

(E) Rats were euthanized by $CO_2$ inhalation.

Frey Method:

Rats are placed in a supine position and a pad is inserted under the dorsal neck to extend the head back toward the supporting surface where the upper surface of the neck is kept horizontal the entire time. Six (6) μl of liquid containing peptide is administered intranasally as drops with a small pipette every 2 min into alternating sides of the nasal cavity (amounting to a four minute interval between doses to the same nostril). Each nostril receives 4 doses of 6 μl of liquid containing peptide, totaling to a combined volume of 48 μl.

If drops are administered to an anesthetized rat more rapidly than what is described above, there is likely to be two problems: first, the rat may have respiratory distress because the drops do not have time to be completely absorbed and end up being aspirated through the nasopharynx into the lungs;

second, there will be less drug delivery due to the fact that previously delivered liquid already covers the nasal mucosa.

*In this experiment, rats are anesthetized with urethane.

FIGS. 1 and 3 demonstrate the dose dependent analgesic efficacy of nasal application of nociceptin, in comparison to intravenous nociceptin, a systemic dose of morphine, or intranasal saline vehicle in the A-delta pain threshold test in rats. The Y axis in FIG. 1 shows the latency to withdrawal of the face (cheek) in response to noxious heating of the cheek at a rate that selectively activates A-delta fiber nociceptors—the pain system component that subtends sharp pain. The Y axis in FIG. 3 shows the latency to withdrawal of the paw in response to noxious heating of the hindpaw at a rate that selectively activates A-delta fiber nociceptors. The X axis indicates how long after administration the analgesic effect lasts after drug application.

FIGS. 2 and 4 demonstrate the dose dependent analgesic efficacy of nasal application of nociceptin, in comparison to intravenous nociceptin, a systemic dose of morphine, or intranasal saline vehicle in the C-fiber pain threshold test in rats. The Y axis in FIG. 2 shows the latency to withdrawal of the face in response to noxious heating of the cheek at a rate that selectively activates C-fiber nociceptors—the pain system component that subtends burning pain. The Y axis in FIG. 4 shows the latency to withdrawal of the paw in response to noxious heating of the paw at a rate that selectively activates C-fiber nociceptors—the pain system component that subtends burning pain. The X axis indicates how long after administration the analgesic effect lasts after drug application.

A clear dose dependent effect was shown for intranasal nociceptin (N/OFQ) in the behavioral response to thermal activation of A-delta and the C-fiber nociceptors in both the face and the paw experiments. Intranasal saline and intravenous nociceptin (N/OFQ) demonstrated no behavioral response to thermal activation of A-delta and the C-fiber nociceptors in both the face and the paw experiments.

Example 3

Effect of Nociceptin Antagonist on Intranasal Nociceptin Induced Reduction of Thermal Nociception This experiment was to verify the binding site of nociceptin induced analgesia in a thermal nociceptive rodent model.

I. Equipment and Materials

Nine male Sprague-Dawley Rats (200-300 g) per arm, nociceptin in saline (50 mg/ml), nociceptin antagonist (SB-612111 {(−)-cis-1-methyl-7-[[4-(2,6-dichlorophenyl)piperidin-1-yl]-methyl]-6,7,8,9-tetrahydro-5H-benzocyclohepten-5-ol}, 100 mg/ml), saline, urethane, A-delta/C algometer, timer.

II. Reference Documents

Same references as in Example 2 and

Chiou L C, Liao Y Y, Fan P C, Kuo P H, Wang C H, Riemer C, Prinssen E P. "Nociceptin/orphanin FQ peptide receptors: pharmacology and clinical implications" *Curr. Drug Targets* (2007) 8(1):117-35.

Spagnolo B, Carra G, Fantin M, Fischetti C, Hebbes C, McDonald J, Barnes T A, Rizzi A, Trapella C, Fanton G, Morari M, Lambert D G, Regoli D, Calo G. "Pharmacological Characterization of the Nociceptin/Orphanin FQ Receptor Antagonist SB-612111 [(−)-cis-1-Methyl-7-[[4-2,6-dichlorophenyl)piperidin-1-yl]methyl]-6,7,8,9-tetrahydro-5H-benzocyclohepten-5-ol]: In Vitro Studies" *JPET* (2007) 321:961-967.

III. Test Articles

Nociceptin in saline, morphine, saline, and nociceptin antagonist (SB-612111).

IV. Test Matrix/Flowchart (A) Groups of six rats per test run were lightly anesthetized with urethane (1.0 g/kg, i.p., titrated to minimal activity in the absence of a stimulus) (Sherman and Loomis et al, 1996). The left and right cheeks and right hindpaw were blackened with India ink to allow even heat distribution.

(B) Each 200-300 g male Sprague-Dawley rat was subjected to varying heat intensities on the left and right check and right hindpaw for selective testing of A-delta vs. C fiber nociception (Yeomans et al., 1996).

For C-fiber testing, the heat intensity was adjusted by altering the supply voltage of a focused projector lamp until a withdrawal latency between 9-13 seconds was observed. The intensity applied (measured in volts) was noted for each animal. To reduce the potential for tissue damage, a cut-off latency of 20 seconds was used after which the stimulus was terminated. Rats not responding up to a supply voltage of 55 volts were excluded from the study.

For A-delta fiber testing, the heat intensity was adjusted until withdrawals occurred at latencies of between 2 and 3 seconds was observed. The intensity applied (measured in volts) was noted for each animal. To reduce potential tissue damage, a cut-off radiation time of 6 seconds was used. Rats not responding up to a voltage of 85 volts were excluded from the study.

(C) Rats received one of the following:

subcutaneous injections of 50 μl nociceptin antagonist in right and left cheeks and right hindpaw (SB-612111, 10.0 mg/kg).

subcutaneous injection of 50 μl saline

Experimenter was blinded as to the nature of substance given.

(D) After waiting 45 minutes, rats were given 48 μl intranasal (Frey Method; Thorne et al., 2004) of nociceptin (50 mg/ml).

(E) Withdrawal latencies were measured in response to radiant heat stimulation of the left and right cheeks, followed by similar measurements of response latencies for each hindpaw. Each animal was tested using its specific radiant amplitude (volts) established in baseline testing. Measurements were taken immediately after dosing and at 15, 30, 45, 60, 90, 120, 150, and 180 min after dosing.

(F) Rats were euthanized by $CO_2$ inhalation.

Figure 5:
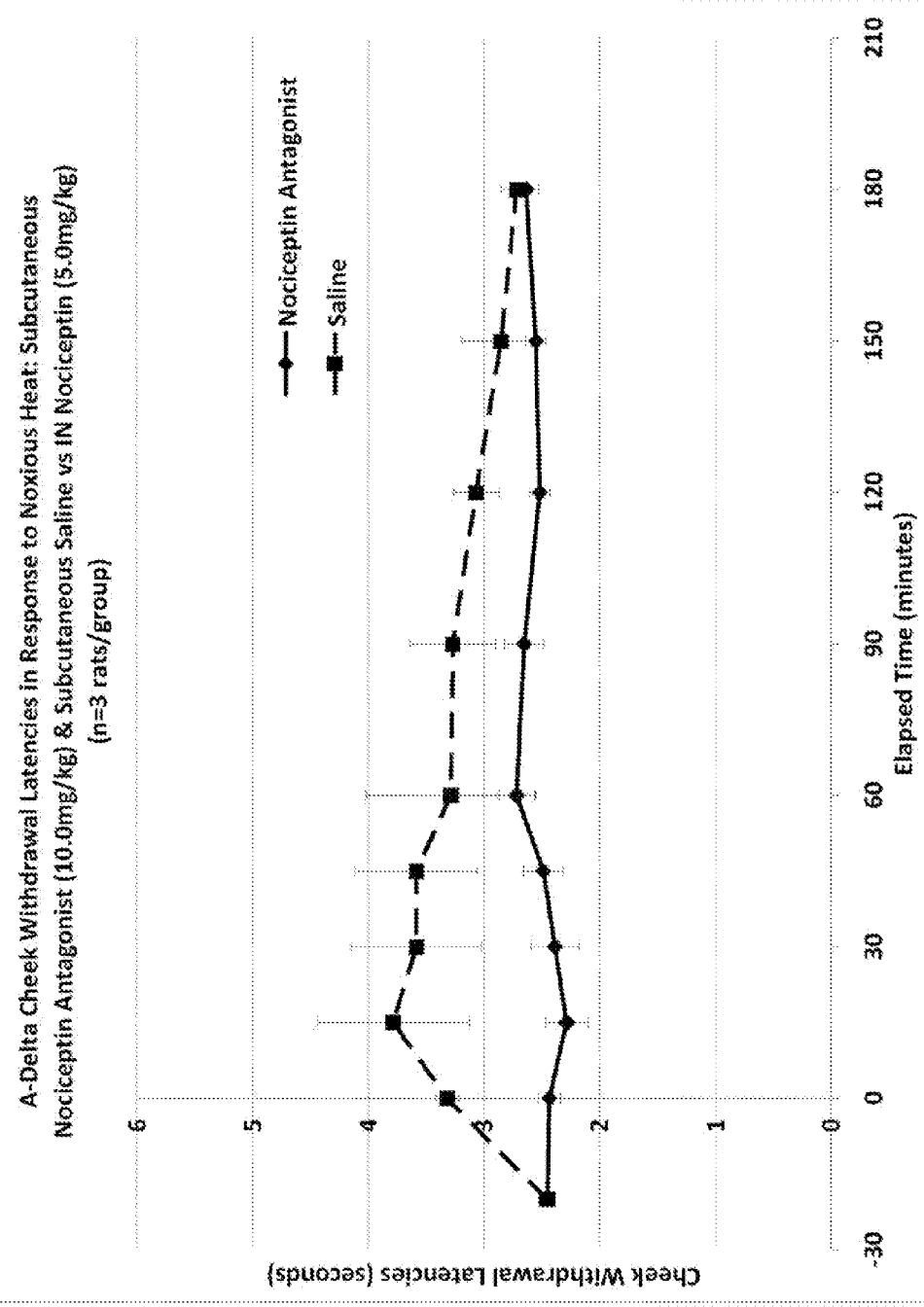
FIG. 5 shows A-delta cheek withdrawal latencies in response to noxious heat: subcutaneous Nociceptin Antagonist (10.0 mg/kg) plus i.n. Nociceptin (5.0 mg/kg) vs. subcutaneous Saline plus i.n. Nociceptin (5.0 mg/kg). Data are presented as the mean±1 SEM. (n=3 rats/group).
Figure 7:
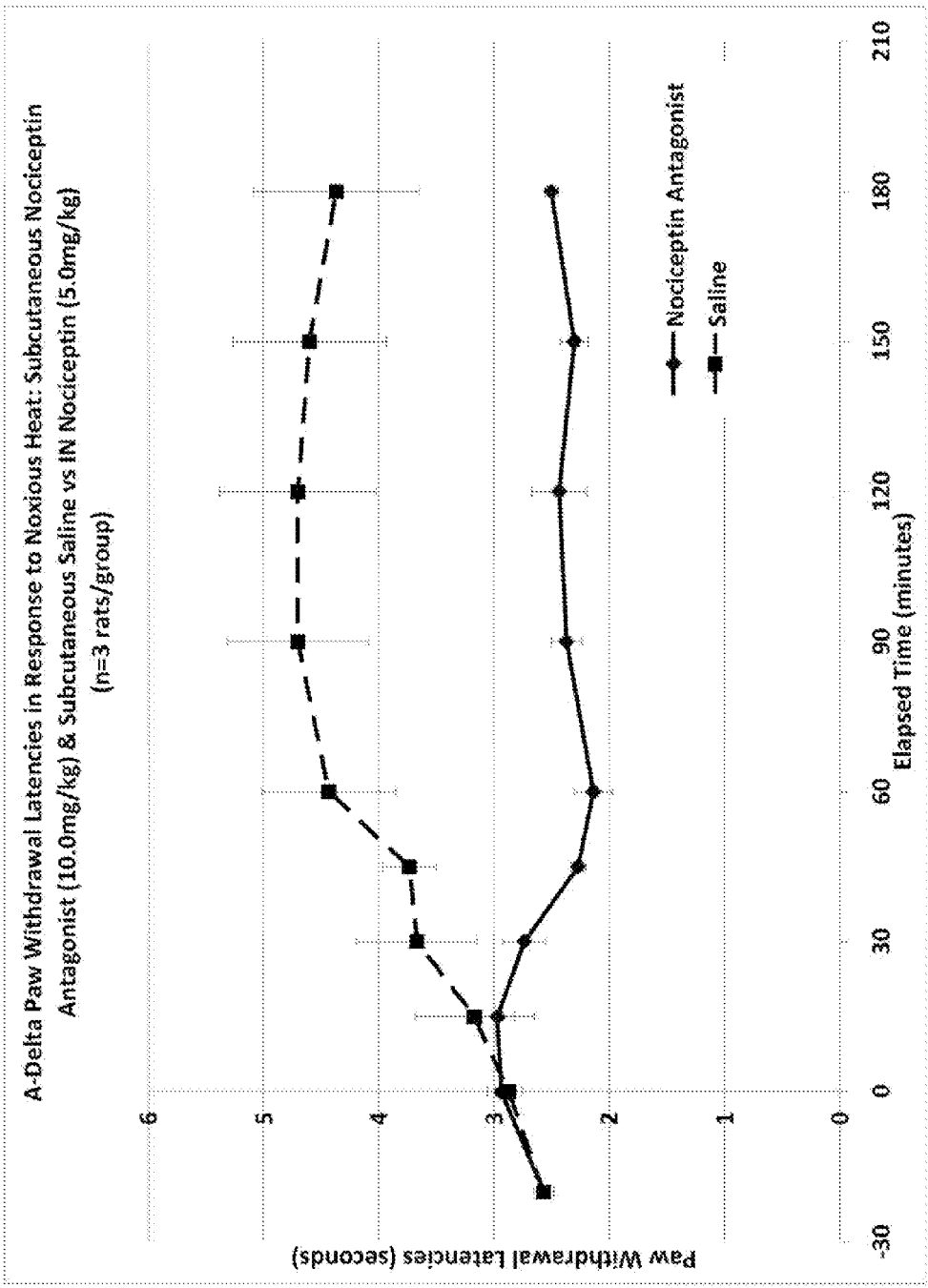
FIG. 7 shows A-delta paw withdrawal latencies in response to noxious heat: subcutaneous Nociceptin Antagonist (10.0 mg/kg) plus i.n. Nociceptin (5.0 mg/kg) vs. subcutaneous Saline plus i.n. Nociceptin (5.0 mg/kg). Data are presented as the mean±1 SEM. (n=3 rats/group).

FIGS. 5 and 7 demonstrate the effect of nociceptin antagonist SB-612111 on intranasal nociceptin induced reduction of thermal nociception in the A-delta pain threshold test. The efficacy of nasal application of nociceptin was measured in rats pretreated with subcutaneous nociceptin antagonist in comparison to rats pre-treated with subcutaneous saline vehicle. The Y axis in FIG. 5 shows the latency to withdrawal of the cheek in response to noxious heating of the cheek at a rate that selectively activates A-delta fiber nociceptors—the pain system component that subtends sharp pain. The Y axis in FIG. 7 shows the latency to withdrawal of the hindpaw in response to noxious heating of the hindpaw at a rate that selectively activates A-delta fiber nociceptors. The X axis indicates how long after administration the analgesic effect lasts after drug application.

Figure 6:
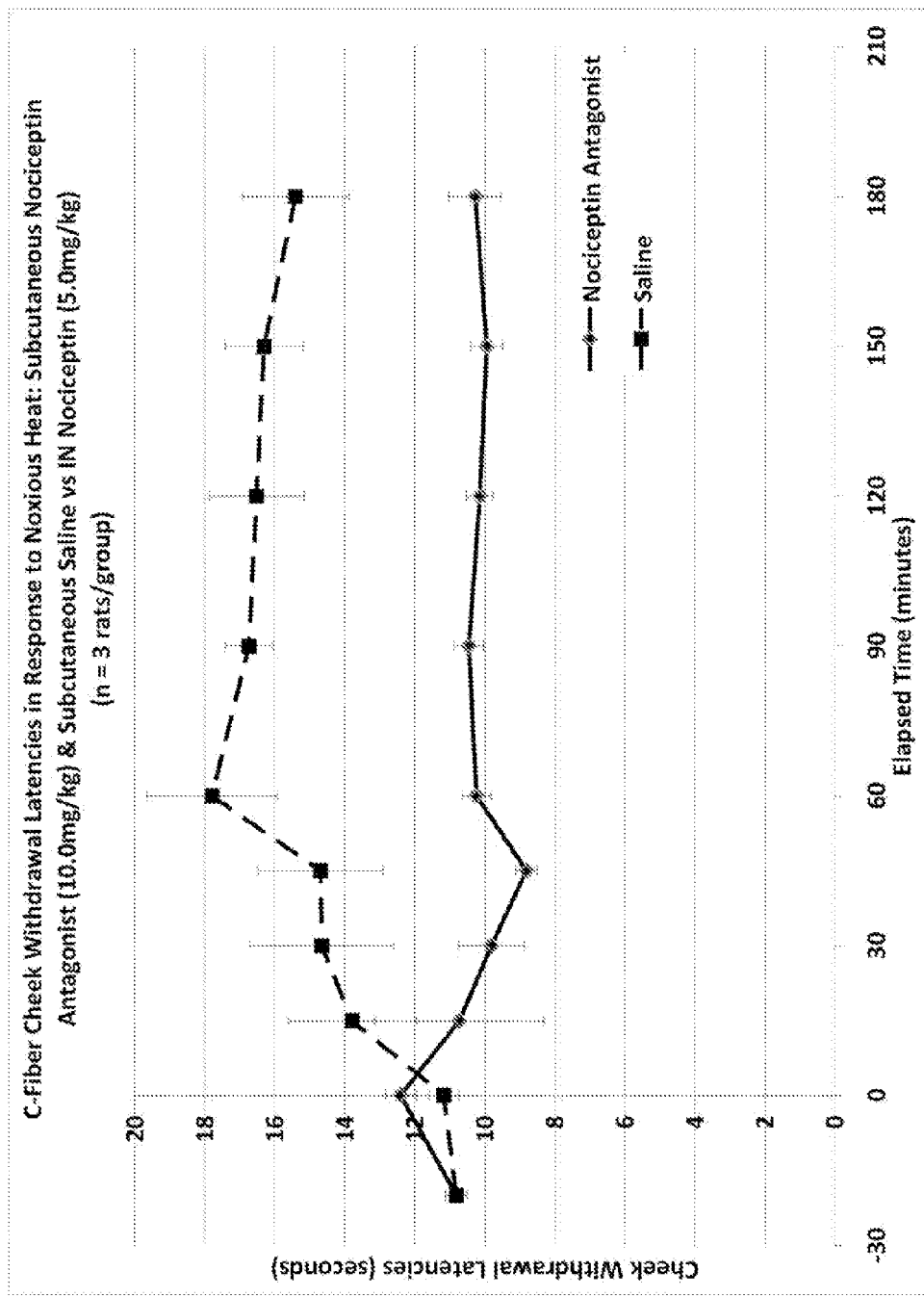
FIG. 6 shows C-fiber cheek withdrawal latencies in response to noxious heat: subcutaneous Nociceptin Antagonist (10.0 mg/kg) plus i.n. Nociceptin (5.0 mg/kg) vs. subcutaneous Saline plus i.n. Nociceptin (5.0 mg/kg). Data are presented as the mean±1 SEM. (n=3 rats/group).
Figure 8:
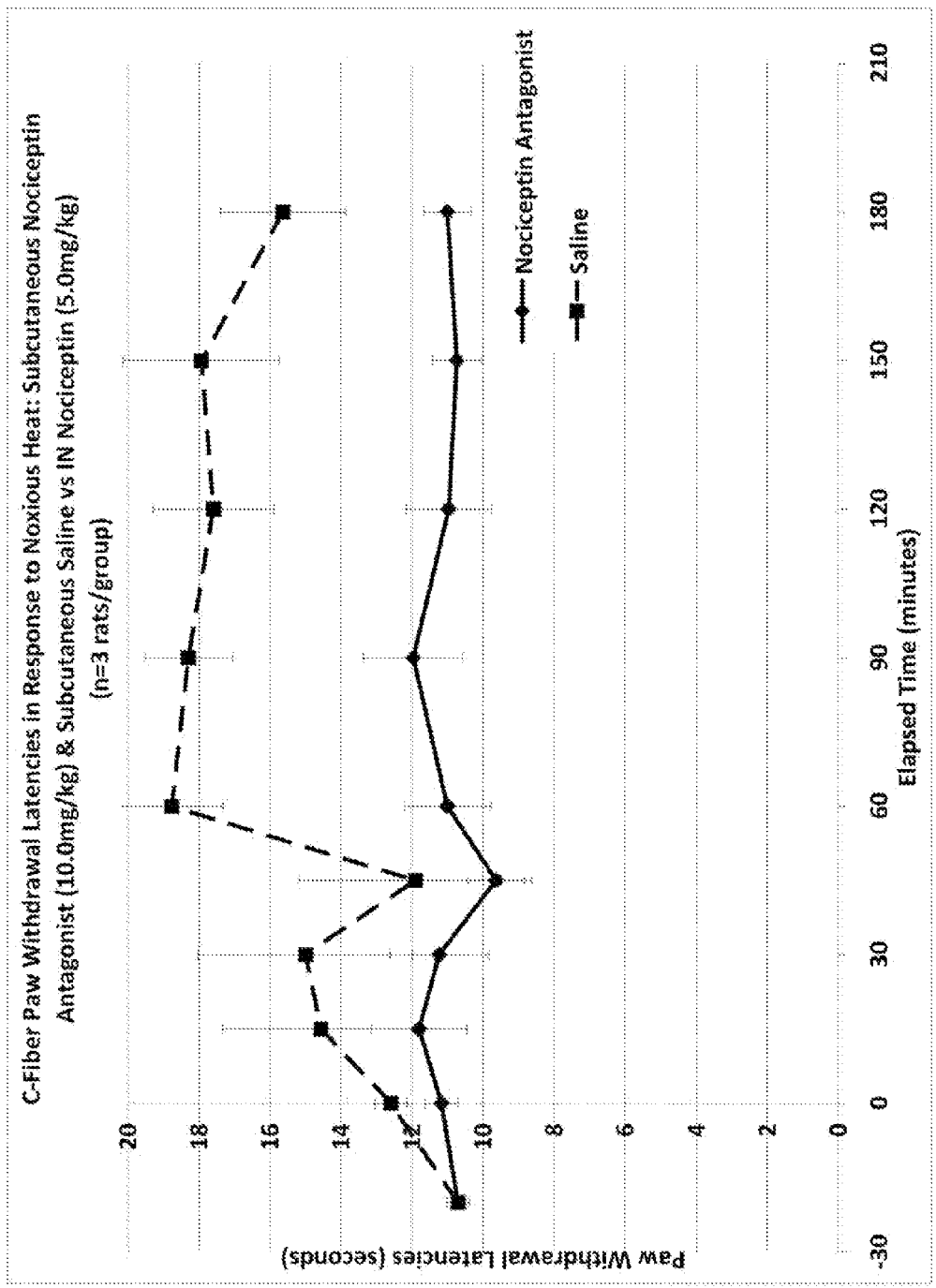
FIG. 8 shows C-fiber paw withdrawal latencies in response to noxious heat: subcutaneous Nociceptin Antagonist (10.0 mg/kg) plus i.n. Nociceptin (5.0 mg/kg) vs. subcutaneous Saline plus i.n. Nociceptin (5.0 mg/kg). Data are presented as the mean±1 SEM. (n=3 rats/group).

FIGS. 6 and 8 demonstrate the effect of nociceptin antagonist SB-612111 on intranasal nociceptin induced reduction of thermal nociception in the C-fiber pain threshold test. The efficacy of nasal application of nociceptin was measured in rats pretreated with subcutaneous nociceptin antagonist in comparison to rats pre-treated with subcutaneous saline vehicle. The Y axis in FIG. 6 shows the latency to withdrawal of the cheek in response to noxious heating of the cheek at a rate that selectively activates C-fiber nociceptors—the pain system component that subtends burning pain. The Y axis in FIG. 8 shows the latency to withdrawal of the hindpaw in response to noxious heating of the hindpaw at a rate that selectively activates C-fiber nociceptors. The X axis indicates how long after administration the analgesic effect lasts after drug application.

The apparent block of the analgesic activity of nociceptin by the nociceptin antagonist suggest that nociceptin induced analgesia is due to binding to the NOP receptor.

Data from these experiments can be analyzed as following: Withdrawal latencies are averaged for cheek and paw responses across animals within a given group. Separate ANOVA's for repeated measures are used to compare A-delta or C fiber mediated cheek and paw withdrawal responses between the saline group and antagonist group.

Example 4

Figure 9:
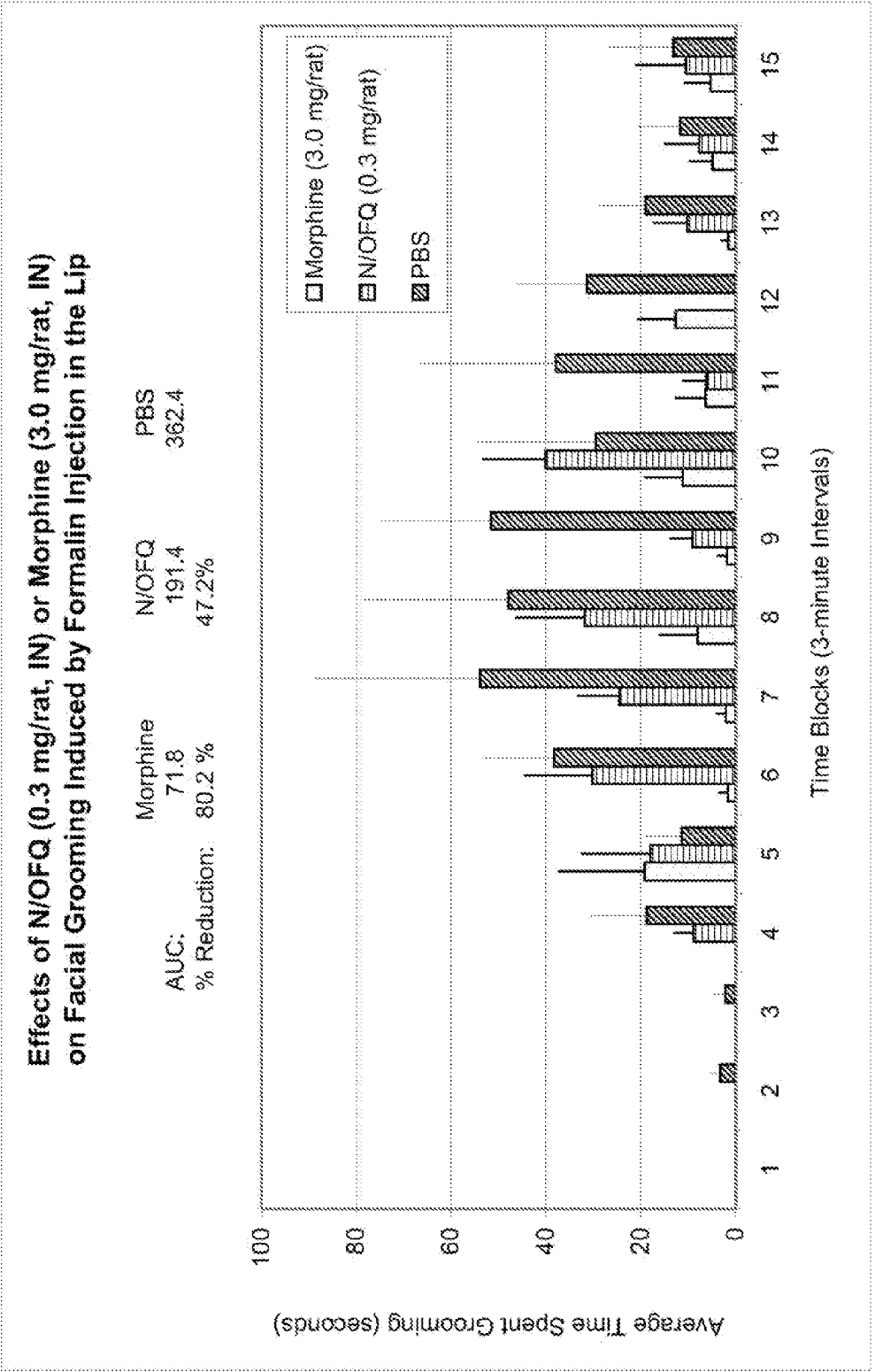
FIG. 9 shows analgesic activity of intranasal N/OFQ in comparison with morphine in response to formalin injection into the lip of male rats. Time spent grooming was determined over 45 minutes and grouped in 3 minute bins. The compounds were administered intranasally at the following doses: morphine 3.0 mg/rat and N/OFQ 0.3 mg/rat. The area under the curve (AUC) for each compound or vehicle was approximated using the trapezodial method. % Reduction= [(Vehicle AUC−Treatment AUC)/Vehicle AUC)]×100%. Data are presented as the mean±1 SEM. (n=6-8 Rats/group).

Antinociceptive Activity of Intranasal N/OFQ in Rodent Model of Facial Tonic Pain The paw formalin model is widely used to assess tonic pain efficacy of putative and known analgesic treatments. We adapted this model to the face in order to assess and compare the effects of intranasal N/OFQ to that of intranasal oxytocin and two benchmarks, sumatriptan (i.p.), and morphine (i.n.). The results of this study demonstrated that 0.1 mg/kg N/OFQ produced a profound (47.2%) inhibition of facial wiping behavior comparable to that produced by 0.1 mg/kg intranasal oxytocin (47.8%) or 42 mg/kg sumatriptan (43.8%). 3 mg/kg morphine produced greater maximal inhibition (80.2%) albeit at a much higher dose (FIG. 9). Thus, intranasal application of N/OFQ produced a robust analgesia in a rodent model of facial tonic pain. Importantly, no sedation or other obvious side-effects were observed in rats receiving N/OFQ.

Example 5

Efficacy of N/OFQ in Incisional Pain Model

To demonstrate utility of N/OFQ in post-surgical pain, we assessed the anti-allodynic activity of intranasal N/OFQ in a rat paw incision model (Brennan, T. J., Vandermeulen, E. P. & Gebhart, G. F. Pain 64, 493-501 (1996)). N/OFQ (5.0 mg/kg) was administered intranasally 24 hours after rats received a small incision on the plantar surface of the hind paw. Effects of intranasal N/OFQ were contrasted with those of intravenous N/OFQ.

Rats were anesthetized with 2.5% isoflurane, after which, the plantar surface of the right hindpaw was treated with provodine-iodine surgical prep. A 5 mm incision was made through the skin and underlying fascia on the plantar surface, close to the hairy/glabrous skin junction. Thereafter, the wound was closed using 2 simple interrupted sutures of 5-0 silk. The wound area was then treated with a triple antibiotic ointment and the animals returned to their home cages (individually housed). Withdrawal thresholds to mechanical stimulation were measured using standard von Frey filaments (TouchTest; Stoelting Co., Wood Dale, Ill., USA), on the right hindpaw prior to and 24 hours following surgery.

For testing, rats were isolated in enclosures with mesh floors (10×10 cm) and allowed to habituate for 15 min. Testing employed the up-down method of Dixon (Dixon, W. J. Staircase bioassay: the up-and-down method. *Neurosci Biobehav Rev* 15, 47-50 (1991)) in order to determine the 50% withdrawal threshold (Chaplan, S. R., Bach, F. W., Pogrel, J. W., Chung, J. M. & Yaksh, T. L. Quantitative assessment of tactile allodynia in the rat paw. *J Neurosci Methods* 53, 55-63 (1994)). Testing began in all rats with the 4.31 filament (2.0 g). The plantar surface of the right hindpaw was stimulated at the incision with the von Frey filament and depending on whether or not there was a withdrawal, the next lowest (withdrawal) or highest (no withdrawal) filament was tested. Testing continued in this manner until 4 responses were scored (regardless of type) after the first withdrawal. 50% thresholds were calculated from the response pattern and the final tested filament. Von Frey monofilaments used (3.61 to 5.18) cover a range of bending forces (0.4-15 g) and diameters (178-483 um) giving applied forces in the range 3.92-147 mN.

Figure 10:
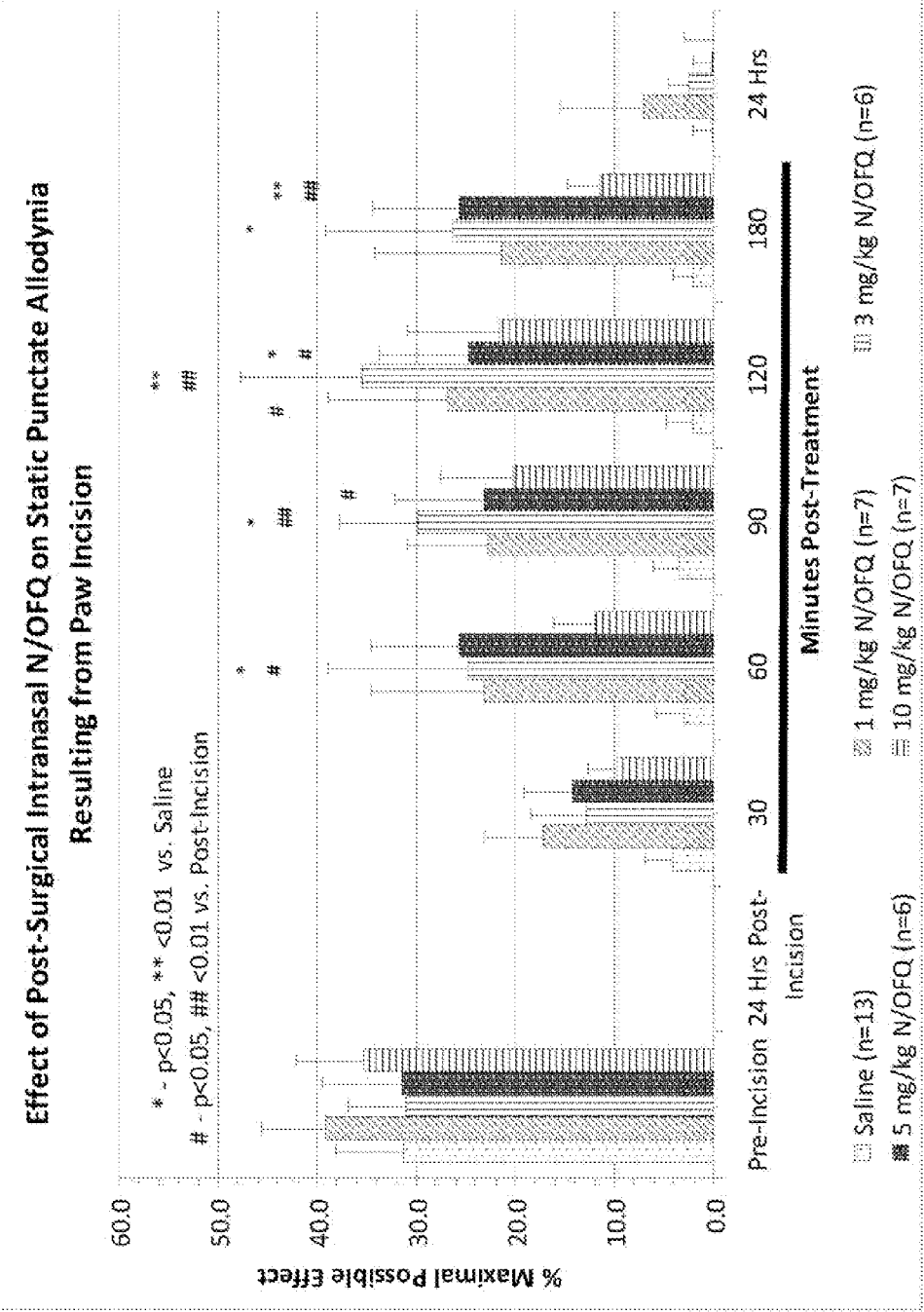
FIG. 10 shows the dose response of post surgical N/OFQ at 1, 3, 5 and 10 mg/kg (i.n.) on punctate allodynia resulting from paw incision. Data are presented as the mean±1 SEM. (n=6-13 Rats/group). * $-p<0.05$ & ** $p<0.01$ compared to Vehicle; #$-p<0.05$ & ## $p<0.01$ compared to Post-surgical value.

The effect is also expressed in % Maximal Possible Effect (% MPE), which is calculated from the 50% thresholds (Treatment Response) as following:

% MPE=[(Treatment Response−Post-Incision Baseline)/(Ceiling Response−Post-Incision Baseline)]×100%;

where the Ceiling Response is 15.0. The dose response graph is shown in FIG. 10.

Figure 11:
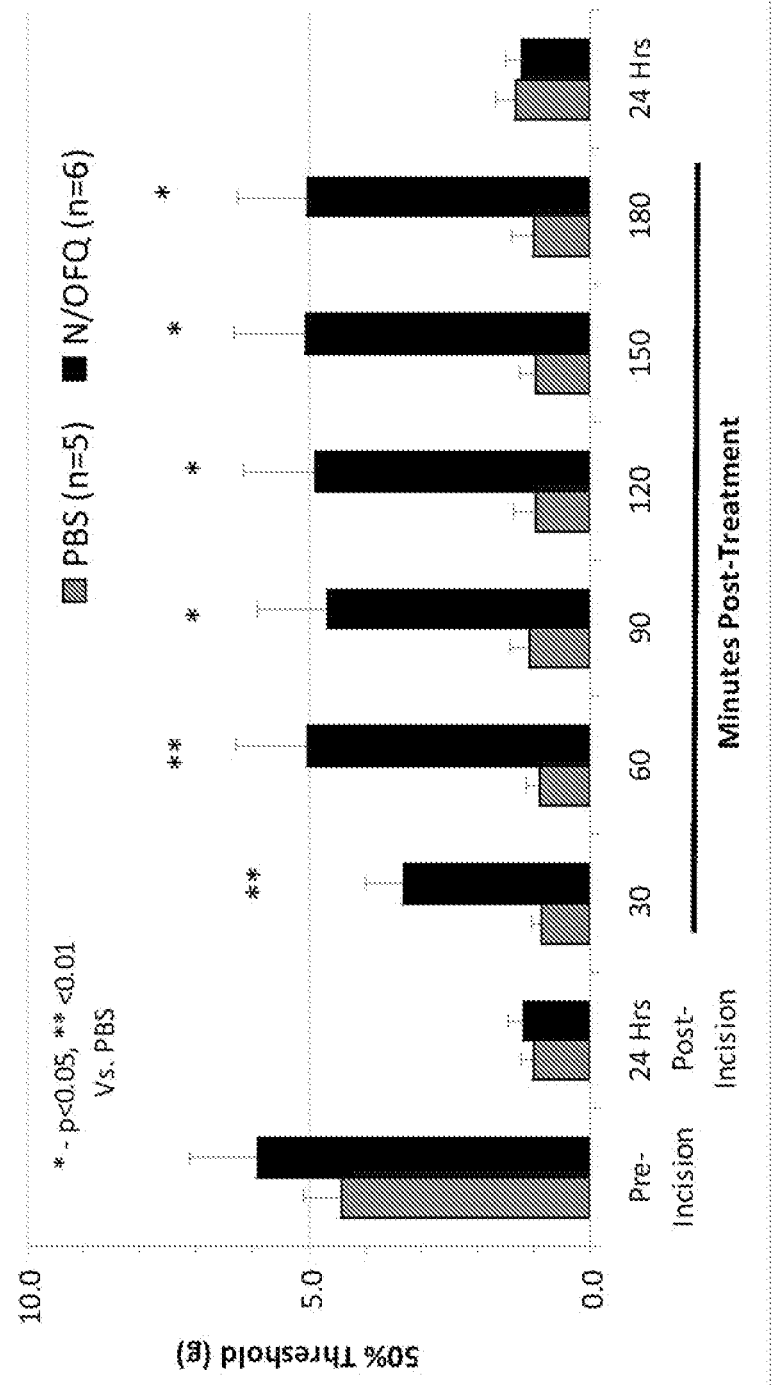
FIGS. 11 and 12 shows the anti-allodynic activity of N/OFQ on responses to static punctate stimuli following surgical incision to the plantar surface of the hind paw of male rats. N/OFQ was administered (FIG. 11) intranasally at 5.0 mg/kg 24 hours following incision or (FIG. 12) intravenously at 5.0 mg/kg 24 hours following incision. 50% threshold withdrawals were determined every 30 minutes following administration using von Frey filaments, employing the up-down technique. Data are presented as the mean±1 SEM. (n=5-6 Rats/group). * $p<0.05$ compared to Vehicle.
Figure 12:
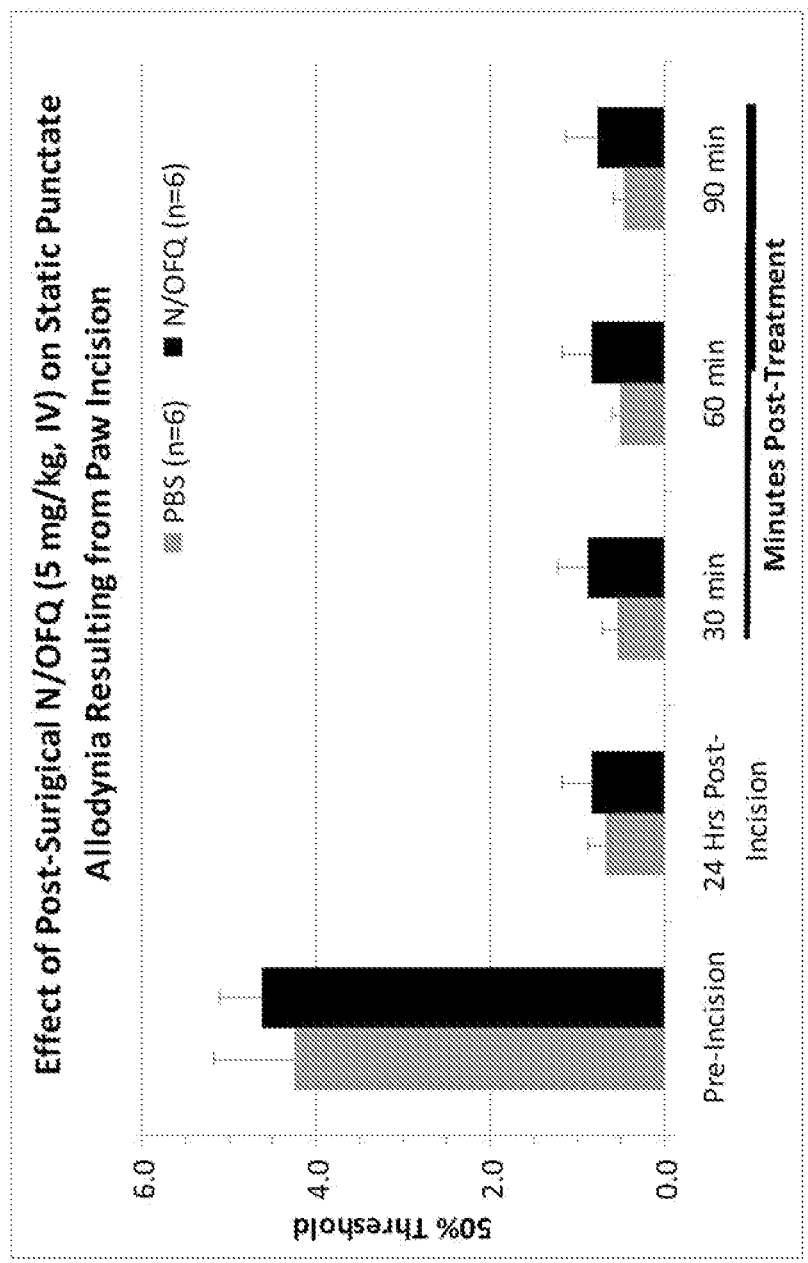

Similar to the results of the thermal stimulus studies, intranasal application of 5.0 mg/kg N/OFQ produced strong anti-allodynic effects (FIG. 11) with a slightly delayed onset (maximum efficacy was reached at 60 minutes). No such reversal of post-surgical allodynia was observed following intravenous application of the same dose of N/OFQ (FIG. 12). These results provide strong evidence that intranasal, but not systemic N/OFQ would be useful in the post-surgical pain setting. This dichotomy again suggests that the effects of intranasally applied N/OFQ are mediated via direct CNS uptake.

Example 6

Efficacy of N/OFQ in Cheek Incisional Pain Model

Figure 13:
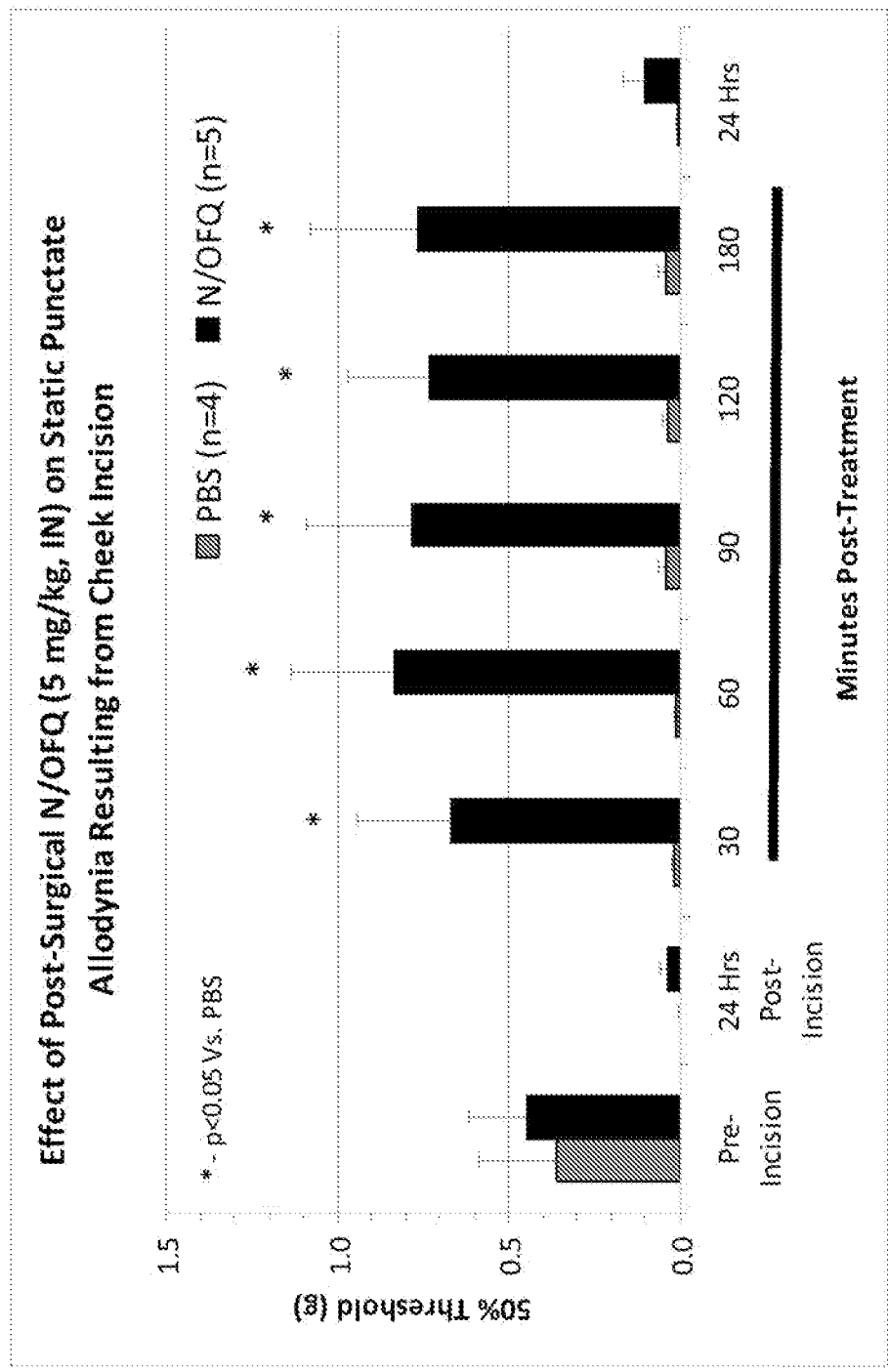
FIG. 13 shows the anti-allodynic activity of N/OFQ on responses to static punctate stimuli following surgical incision to the cheek of male rats. N/OFQ (5 mg/kg, i.n.) was administered 24 hours following incision. 50% threshold withdrawals were determined every 30 minutes following administration using von Frey filaments, employing the up-down technique. Data are presented as the mean±1 SEM. (n=4-5 Rats/group). * $-p<0.05$ compared to Vehicle.

FIG. 13 shows the effect of post-surgical N/OFQ (5 mg/kg, i.n.) on static punctate allodynia resulting from cheek incision. N/OFQ was administered intranasally at 5.0 mg/kg 24 hours following a single 5 mm percutaneous incision (including the underlying muscle) on the shaved cheek. Surgery was performed under 2.5% isoflurane anesthesia and the incision closed using a simple interrupted suture of 5-0 silk. 50% threshold withdrawals were determined every 30 minutes following administration using von Frey filaments (TouchTest; Stoelting Co., Wood Dale, Ill., USA), employing the up-down technique of Dixon. This model was adapted from the plantar hind paw incisional model (Brennan, T. J., Vandemmeulen, E. P. & Gebhart, G. F. (1996) Pain 64; 493-501), by placing rats in Broome restrainers and employing lighter testing filaments. Von Frey monofilaments used for cheek testing cover a range of bending forces (0.008-1.4 g) and diameters (64-254 um) giving applied forces in the range 0.078-13.72 mN.

Figure 14:
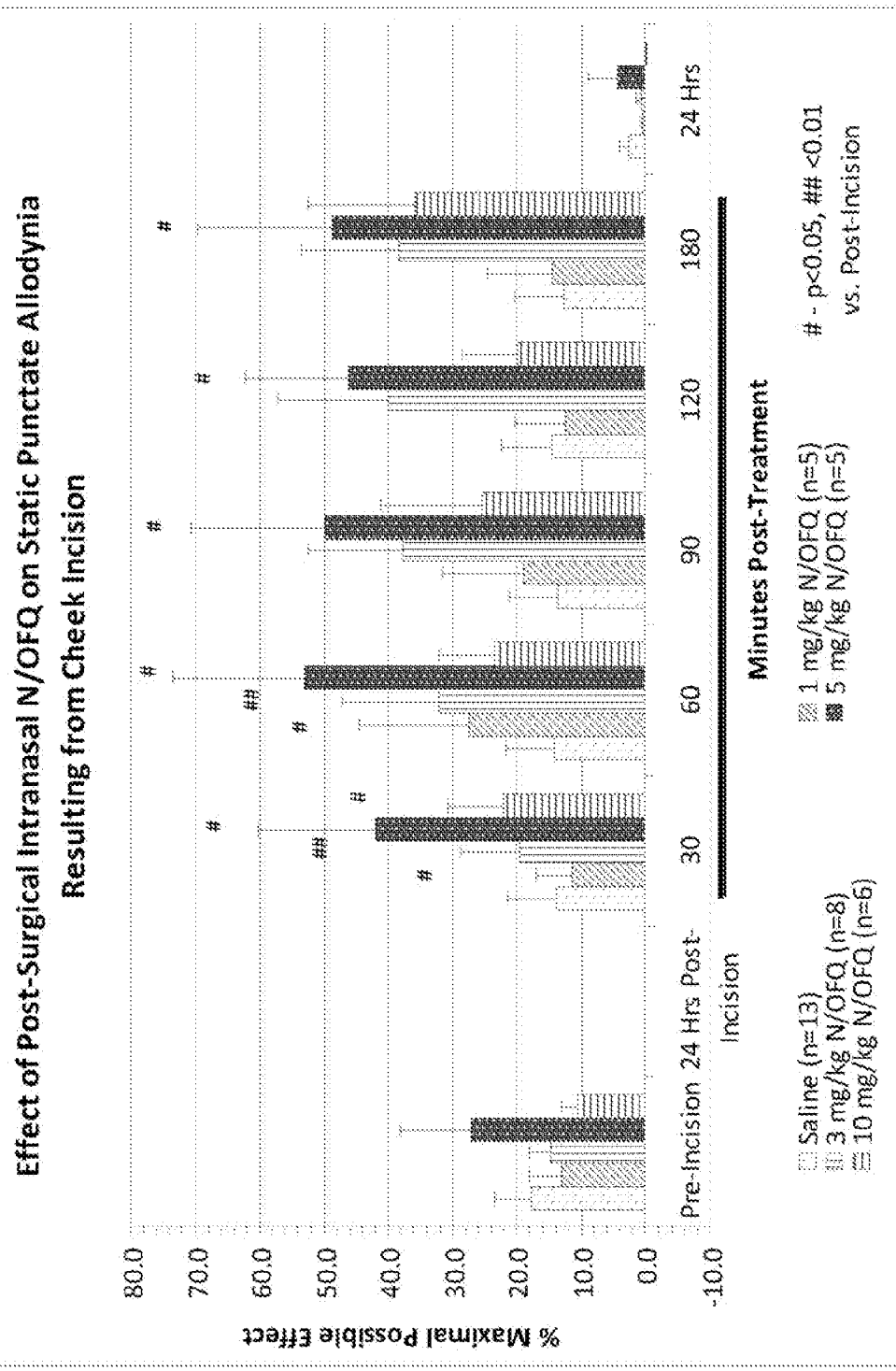
FIG. 14 shows the dose response of post surgical N/OFQ at 1, 3, 5 and 10 mg/kg (i.n.) on punctate allodynia resulting from cheek incision. Data are presented as the mean±1 SEM. (n=5-13 Rats/group). #$-p<0.05$ & ## $p<0.01$ compared to Post-surgical value.
Figure 15:
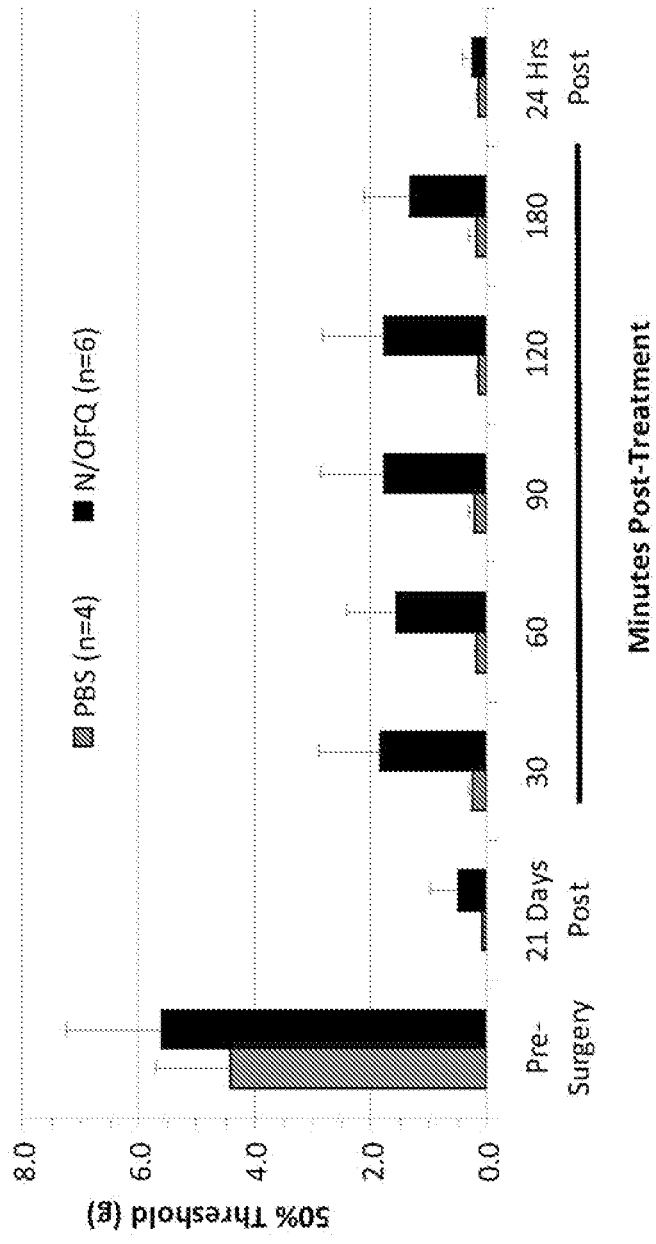
FIG. 15 shows the anti-allodynic activity of N/OFQ on responses to static punctate stimuli following Spared Nerve Injury in male rats. N/OFQ was administered intranasally at 5.0 mg/kg 21 days following surgery. 50% threshold withdrawals were determined every 30 minutes following administration using von Frey filaments, employing the up-down technique. Data are presented as the mean±1 SEM. (n=4-6 Rats/group).
Figure 16:
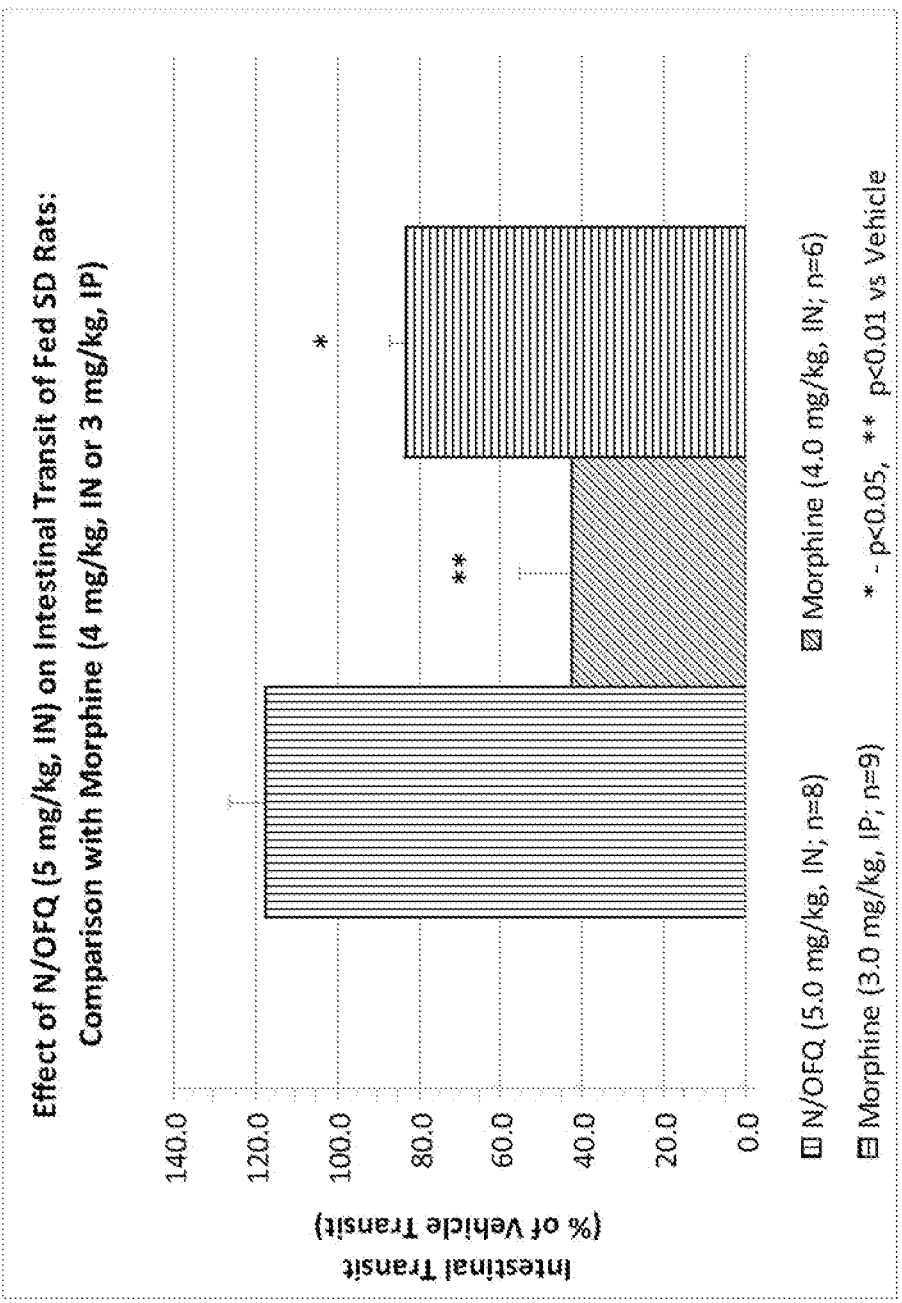
FIG. 16 shows intestinal transit as % of vehicle response following intranasal N/OFQ (5.0 mg/kg), intranasal morphine (4.0 mg/kg), or intraperitoneial morphine (3.0 mg/kg). Compounds were administered 20-30 minutes prior to the charcoal meal (2 mL/rat). Rats were sacrificed 30 minutes after receiving the meal. % transit was calculated as the ratio of the travel distance of the charcoal marker divided by the full length of the small intestine multiplied by 100%. Data are presented as the mean±1 SEM. (n=8 Rats/group).

The effect is also expressed in % Maximal Possible Effect (% MPE), which is calculated from the 50% thresholds (Treatment Response) as following:

% MPE=[(Treatment Response−Post-Incision Baseline)/(Ceiling Response−Post-Incision Baseline)]×100%;

where the Ceiling Response is 1.5. A dose response graph is shown in FIG. 14.

Example 7

Spared Nerve Injury Model

The anti-allodynic activity of N/OFQ was assessed using a standard nerve injury model in the rat, the spared nerve injury model (Decosterd, I. & Woolf, C. J. Pain 87:149-58 (2000)). Surgical transection of two of the three branches of the sciatic nerve of one leg produces a hypersensitivity of the plantar surface of the ipsilateral hindpaw. The model reproduces many of the characteristics of neuropathic pain conditions; e.g. apparent hypersensitivity to pain, but, as with the spinal nerve injury, no signs of tonic, ongoing distress.

Methods:

Surgery was conducted under isoflurane (3.5%) anesthesia. Once a plane of deep anesthesia was achieved, the skin on the lateral surface of the thigh was shaved and prepped with a providine-iodine solution. Skin was incised and a section made directly through the biceps femoris muscle exposing the sciatic nerve and its three terminal branches: the sural, common peroneal and tibial nerves. The tibial and common peroneal nerves were then cut and ligated (proximal to the axotomy) with 5.0 silk, leaving the sural nerve intact, but removing 2-4 mm of the distal nerve stumps. Care was taken to avoid any contact with, or stretching of, the intact sural nerve. Muscle and skin were then closed in two layers and the wound site was treated with antibiotic ointment. Following surgery, animals were given 0.05 mg/kg buprenorphine 1M, as a post-surgical analgesic.

To assess the effects of nerve injury on nociceptive sensitivity, mechanical allodynia was measured using von Frey monofilaments (TouchTest; Stoelting Co., Wood Dale, Ill., USA), applied to the plantar hindpaw ipsilateral to the injury and were assessed before and after injury, and before and after intranasal N/OFQ. Testing employed the up-down method of Dixon in order to determine the 50% withdrawal threshold. Von Frey monofilaments used for testing cover a range of bending forces (0.008-15 g) and diameters (61-483 um) giving applied forces in the range 0.078-147 mN.

Results:

Nerve injury produced dramatic allodynia in the paw ipsilateral to the injury within 6 days of the surgery. N/OFQ (5.0 mg/kg) was administered intranasally 21 days after the nerve injury, and produced strong anti-allodynic effects in the ipsilateral paw over the entire 3-hour testing session (FIG. 13). These effects were no longer apparent the following day, 24 hours after receiving the compound. Despite the small sample size (Vehicle: n=4 & N/OFQ: n=6), there was still a clear trend toward efficacy.

These results provide strong evidence that intranasal N/OFQ will be useful in treating conditions of neuropathic pain, in addition to primary pain states.

Example 8

Effect of N/OFQ on Gastric Transit Time

One of the major complications associated with giving opiate analgesics, such as morphine, to control pain is constipation. In rats, this constipation is observed as an increase in gut transit time. In order to determine whether intranasasal N/OFQ, which has a similar analgesic efficacy to that of strong opiates, would also produce constipation, the effects of intranasal N/OFQ on gastric transit time was assessed. Intestinal transit time (ITT) was assessed in rats pretreated with N/OFQ (5.0 mg/kg, i.n.) and given a charcoal meal (12.5% activated charcoal in a 12.5% gum arabic suspension (Tavani, A., Petrillo, P., La Regina, A. & Sbacchi, M. Role of peripheral mu, delta and kappa opioid receptors in opioid-induced inhibition of gastrointestinal transit in rats. *J Pharmacol Exp Ther* 254, 91-97 (1990)). Effects were contrasted against the effects of either intraperitoneal (3.0 mg/kg) or intranasal (4.0 mg/kg) morphine. Briefly, rats were given ad lib access to standard chow and water overnight and then received the test compound the following morning. 20 to 30 minutes later, rats received an oral gavage of the charcoal suspension (2 mL) and after an additional 30 minutes were euthanized by carbon dioxide inhalation. Stomach and small intestine were immediately removed and both the total length of small intestine and the distance traveled by the charcoal were recorded. Percent transit was calculated as the ratio of charcoal distance divided by total small intestine length multiplied by 100%. For comparison across studies, compound effects were also expressed as percent of transit observed in the vehicle treated group (100%−((Mean Vehicle % Transit−Drug % Transit)/Mean Vehicle % Transit)). While morphine produced considerable slowing of transit (decreased percent transit) regardless of route of administration, no such effects were observed in rats pretreated with N/OFQ (FIG. 14). These data provide strong evidence that despite producing robust analgesic effects comparable to morphine, intranasal N/OFQ is unlikely to produce constipation in clinical settings.

Example 9

Preliminary Behavioral Assessments after Intranasal N/OFQ Dosing

As clinically available strong analgesics are known to have sometimes profound behavioral toxicological effects (i.e., sedation), it is critical to determine if N/OFQ is similarly burdened. Thus, preliminary behavioral toxicological screening was initiated for intranasally administered N/OFQ. Briefly, 4 rats were administered 25 mg/kg of N/OFQ intranasally and returned to their home cages (single housing) and allowed to recover from anesthesia. Observations were made every 20 minutes for the first hour and hourly thereafter and any abnormal findings were recorded. 24 hours after receiving N/OFQ, rats were again observed for any delayed toxicological responses. General activity was subjectively determined and the presence of any of the following behaviors was recorded: tonic/clonic movements, ataxia, stereotypies, vocalizations, lacrimation, salivation, piloerection, ptosis, and abnormal respirations. Additionally, any abnormal responses to handling the animal or to approaching or touching the animal were scored as stimulus reactivity. No abnormal responses were observed for acute doses up to 5-fold greater than the efficacious dose determined in the thermal heating and post-incisional models (5 mg/kg).

Although the foregoing invention has been described in some detail by way of illustration and example for purposes of clarity of understanding, it will be apparent to those skilled in the art that certain changes and modifications may be practiced without departing from the invention. Therefore, the descriptions and examples should not be construed as limiting the scope of the invention.

It should be noted that, as used herein, the singular form "a", "an", and "the" includes plural references unless indicated otherwise. Additionally, as used herein, the term "comprising" and its cognates are used in their inclusive sense; that is, equivalent to the term "including" and its corresponding cognates.

All patents, patent applications, documents, and articles cited herein are incorporated by reference in their entireties.

What is claimed is:

1. A method for the treatment of pain comprising administering to an individual in need thereof an effective dose of a non-opioid peptide NOP agonist via intranasal administration, provided when the pain is a trigeminal nerve-associated pain, the non-opioid peptide NOP agonist is not co-administered with an oxytocin peptide.

2. The method of claim 1, wherein said treatment comprises treatment of a trigeminal pain, a somatic pain, a neuropathic pain or a visceral pain.

3. The method of claim 2, wherein said treatment comprises treatment of a somatic pain.

4. The method of claim 2, wherein said treatment comprises treatment of a neuropathic pain.

5. The method of claim 2, wherein said treatment comprises treatment of a visceral pain.

6. The method of claim 1, wherein said treatment comprises treatment of an acute pain or a chronic pain.

7. The method of claim 1, wherein the pain is a craniofacial pain or a head pain.

8. The method of claim 7, wherein the craniofacial pain or the head pain is caused by temporomandibular joint disorder (TMJ), migraine or trigeminal neuralgia.

9. The method of claim 8, wherein the craniofacial pain or the head pain is caused by temporomandibular joint disorder (TMJ).

10. The method of claim 8, wherein the craniofacial pain or the head pain is caused by migraine.

11. The method of claim 8, wherein the craniofacial pain or the head pain is caused by trigeminal neuralgia.

12. The method of claim 1, wherein said treatment comprises treatment of a somatic pain, a neuropathic pain or a visceral pain.

13. The method of claim 12, wherein the non-opioid peptide NOP agonist is not co-administered with an oxytocin peptide.

14. The method of claim 1, wherein the non-opioid peptide NOP agonist is selected from the group consisting of N/OFQ, truncated N/OFQ analogs, N/OFQ agonist peptides and NOP agonist hexapeptides.

15. The method of claim 14, wherein the non-opioid peptide NOP agonist is a truncated N/OFQ analog.

16. The method of claim 1, further comprising administering to the individual in need thereof at least one additional active agent, wherein the additional active agent is administered before, after or simultaneously with administration of the non-opioid peptide NOP agonist.

17. The method of claim 16, wherein the additional active agent is selected from the group consisting of non-peptide opioids, opioid and opioid-like peptides and their analogs, NMDA-receptor antagonists, sodium channel blockers, calcium channel blockers, adrenergic antagonists, gabaergic agonists, glycine agonists, cholinergic agonists, adrenergic agonists, epinephrine, anticonvulsants, Rho kinase inhibitors, PKC inhibitors, p38-MAP kinase inhibitors, ATP receptor blockers, endothelin receptor blockers, chemokines, interleukin and tumor necrosis factor blockers, pro-inflammatory cytokines, tricyclic antidepressants, serotonergic antagonists, serotonergic agonists, NSAIDs and COXIBs, acetaminophen, analgesic peptides, toxins, TRP channel agonists and antagonists, cannabanoids, antagonists of pro-nociceptive peptide neurotransmitter receptors CGRP1 and CGRP2, antagonists of pro-nociceptive peptide neurotransmitter receptor NK1, antagonists of pro-nociceptive peptide neurotransmitter receptor NK2, antagonists of pro-nociceptive peptide neurotransmitter receptor Y1-5, antagonists of pro-nociceptive peptide neurotransmitter receptors VPAC2, VPAC1 or PAC1, antagonists of pro-nociceptive peptide neurotransmitter receptors Gal1-3 or GalR1-3, agonists or antagonists of vasopressin, corticotropin releasing hormone (CRH), growth hormone releasing hormone (GHRH), luteinizing hormone releasing hormone (LHRH), somatostatin growth hormone release inhibiting hormone, thyrotropin releasing hormone (TRH), glial-derived neurotrophic factor (GDNF), brain-derived neurotrophic factor (BDNF), nerve growth factor (NGF), neurotrophin-3 (NT-3), pancreatic polypeptide, peptide tyrosine-tyrosine, glucogen-like peptide-1 (GLP-1), peptide histidine isoleucine (PHI), pituitary adenylate cyclase activating peptide (PACAP), brain natriuretic peptide, cholecystokinin (CCK), islet amyloid polypeptide (IAPP) or amylin, melanin concentrating hormone (MCH), melanocortins (ACTH, α-MSH and others), neuropeptide FF (F8Fa), neurotensin, parathyroid hormone related protein, calcitonin, Agouti gene-related protein (AGRP), cocaine and amphetamine regulated transcript (CART)/peptide, 5-HT-moduline, hypocretins/orexins, nocistatin, prolactin releasing peptide, secretoneurin, urocortin and derivatives and analogues thereof.

18. The method of claim 1, wherein the non-opioid peptide NOP agonist is administered as a pharmaceutical composition.

19. The method of claim 18, wherein the pharmaceutical composition further comprises at least one additional active agent.

20. The method of claim 18, wherein the pharmaceutical composition further comprises one or more additional active agents selected from the group consisting of non-peptide opioids, opioid and opioid-like peptides and their analogs, NMDA-receptor antagonists, sodium channel blockers, calcium channel blockers, adrenergic antagonists, gabaergic agonists, glycine agonists, cholinergic agonists, adrenergic agonists, epinephrine, anticonvulsants, Rho kinase inhibitors, PKC inhibitors, p38-MAP kinase inhibitors, ATP receptor blockers, endothelin receptor blockers, chemokines, interleukin and tumor necrosis factor blockers, pro-inflammatory cytokines, tricyclic antidepressants, serotonergic antagonists, serotonergic agonists, NSAIDs and COXIBs, acetaminophen, analgesic peptides, toxins, TRP channel agonists and antagonists, cannabanoids, antagonists of pro-nociceptive peptide neurotransmitter receptors CGRP1 and CGRP2, antagonists of pro-nociceptive peptide neurotransmitter receptor NK1, antagonists of pro-nociceptive peptide neurotransmitter receptor NK2, antagonists of pro-nociceptive peptide neurotransmitter receptor Y1-5, antagonists of pro-nociceptive peptide neurotransmitter receptors VPAC2, VPAC1 or PAC1, antagonists of pro-nociceptive peptide neurotransmitter receptors Gal1-3 or GalR1-3, agonists or antagonists of vasopressin, corticotropin releasing hormone (CRH), growth hormone releasing hormone (GHRH), luteinizing hormone releasing hormone (LHRH), somatostatin growth hormone release inhibiting hormone, thyrotropin releasing hormone (TRH), glial-derived neurotrophic factor (GDNF), brain-derived neurotrophic factor (BDNF), nerve growth factor (NGF), neurotrophin-3 (NT-3), pancreatic polypeptide, peptide tyrosine-tyrosine, glucogen-like peptide-1 (GLP-1), peptide histidine isoleucine (PHI), pituitary adenylate cyclase activating peptide (PACAP), brain natriuretic peptide, cholecystokinin (CCK), islet amyloid polypeptide (IAPP) or amylin, melanin concentrating hormone (MCH), melanocortins (ACTH, α-MSH and others), neuropeptide FF (F8Fa), neurotensin, parathyroid hormone related protein, calcitonin, Agouti gene-related protein (AGRP), cocaine and amphetamine regulated transcript (CART)/peptide, 5-HT-moduline, hypocretins/orexins, nocistatin, prolactin releasing peptide, secretoneurin, urocortin and derivatives and analogues thereof.

21. The method of claim 18, wherein the pharmaceutical composition further comprises one or more pharmaceutically acceptable excipients, adjuvants, diluents or stabilizers.

22. The method of claim 18, wherein the pharmaceutical composition further comprises at least one protease inhibitor and/or at least one absorption enhancer.

23. The method of claim 18, wherein the non-opioid peptide NOP agonist is selected from the group consisting of N/OFQ, truncated N/OFQ analogs, N/OFQ agonist peptides and NOP agonist hexapeptides.

24. The method of claim 23, wherein the non-opioid peptide NOP agonist is a truncated N/OFQ analog.

25. The method of claim 1, wherein the non-opioid peptide NOP agonist is N/OFQ and the unit dose of the N/OFQ administered is about 0.2 mg to about 5000 mg.

26. The method of claim 1, wherein the administration results in reduction of a pain rating on the VAS of 30% or more.

* * * * *